United States Patent
Eriksson et al.

(10) Patent No.: US 7,341,996 B2
(45) Date of Patent: *Mar. 11, 2008

(54) PROCESSED VASCULAR ENDOTHELIAL GROWTH FACTOR-B POLYPEPTIDES

(75) Inventors: Ulf Eriksson, Bålsta (SE); Birgitta Olofsson, Stockholm (SE); Kari Alitalo, Espoo (FI); Katri Pajusola, Helsinki (FI)

(73) Assignees: Ludwig Institute for Cancer Research, New York, NY (US); Licentia Ltd., Helsinki (FI)

(*) Notice: Subject to any disclaimer, the term of this patent is extended or adjusted under 35 U.S.C. 154(b) by 247 days.

This patent is subject to a terminal disclaimer.

(21) Appl. No.: 10/948,736

(22) Filed: Sep. 24, 2004

(65) Prior Publication Data

US 2005/0064493 A1   Mar. 24, 2005

Related U.S. Application Data

(60) Continuation of application No. 09/961,756, filed on Sep. 25, 2001, now abandoned, which is a division of application No. 08/851,896, filed on May 6, 1997, now Pat. No. 6,331,301, which is a division of application No. 08/469,427, filed on Jun. 6, 1995, now Pat. No. 5,607,918, which is a continuation-in-part of application No. 08/397,651, filed on Mar. 1, 1995, now abandoned, said application No. 09/961,756 is a continuation of application No. 08/609,443, filed on Mar. 1, 1996, now Pat. No. 5,840,693, which is a continuation-in-part of application No. 08/569,063, filed on Dec. 6, 1995, now Pat. No. 5,928,939, which is a continuation-in-part of application No. 08/469,427, filed on Jun. 6, 1995, now Pat. No. 5,607,918.

(51) Int. Cl.
*A61K 38/18* (2006.01)
*C07K 14/515* (2006.01)

(52) U.S. Cl. .................. 514/12; 530/350; 530/399

(58) Field of Classification Search .................. None
See application file for complete search history.

(56) References Cited

U.S. PATENT DOCUMENTS

| | | | |
|---|---|---|---|
| 4,456,550 A | 6/1984 | Dvorak et al. | |
| 4,659,678 A | 4/1987 | Forrest et al. | |
| 5,036,003 A | 7/1991 | Olander et al. | |
| 5,240,848 A | 8/1993 | Keck et al. | |
| 5,607,918 A | 3/1997 | Eriksson et al. | |
| 5,726,152 A | 3/1998 | Bayne et al. | |
| 5,928,939 A | 7/1999 | Eriksson et al. | |

FOREIGN PATENT DOCUMENTS

| | | |
|---|---|---|
| WO | WO 95/24473 | 9/1995 |
| WO | WO 96/27007 | 9/1996 |
| WO | WO 96/39421 | 12/1996 |

OTHER PUBLICATIONS

Olofsson et al., "Vascular Endothelial Growth Factor B, a Novel Growth Factor Endothelial Cells", Proc. Natl. Acad. Sci. USA, vol. 93, pp. 2576-2581 (1996).

Orlandini et al., "Identification of a c-fos-Induced Gene That is Related to the Platelet-Derived Growth Factor/Vascular Endothelial Growth Factor Family", Proc. Natl. Acad. Sci. USA, vol. 93, pp. 11675-11680 (1996).

*Primary Examiner*—Marianne P. Allen
(74) *Attorney, Agent, or Firm*—Crowell & Moring LLP

(57) ABSTRACT

VEGF-B polypeptides from the PDGF family of growth factors having the property of promoting mitosis and proliferation of vascular endothelial cells, DNA sequences encoding these polypeptides, pharmaceutical compositions containing them and antibodies which react with them. The VEGF-B polypeptides are useful in stimulating angiogenesis as well as in diagnostic applications.

16 Claims, 13 Drawing Sheets

Figure 1
Deduced amino acid sequence of 1st reading frame of cDNA clone

```
  1                                                              CG
     Gly Arg Pro Val Val Pro Trp Ile Asp Val Tyr Ala Arg Ala Thr Cys Gln    17
  3  GGA CGC CCA GTG GTG CCA TGG ATA GAC GTT TAT GCA CGT GCC ACA TGC CAG
     Pro Arg Glu Val Val Val Pro Leu Ser Met Glu Leu Met Gly Asn Val Val   34
 55  CCC AGG GAG GTG GTG GTG CCT CTG AGC ATG GAA CTC ATG GGC AAT GTG GTC
     Lys Gln Leu Val Pro Ser Cys Val Thr Val Gln Arg Cys Gly Gly Cys Cys   51
106  AAA CAA CTA GTG CCC AGC TGT GTG ACT GTG CAG CGC TGT GGT GGC TGC TGC
     Pro Asp Asp Gly Leu Glu Cys Val Pro Thr Gly Gln His Gln Val Arg Met   68
157  CCT GAC GAT GGC CTG GAA TGT GTG CCC ACT GGG CAA CAC CAA GTC CGA ATG
     Gln Ile Leu Met Ile Gln Tyr Pro Ser Ser Gln Leu Gly Glu Met Ser Leu   85
208  CAG ATC CTC ATG ATC CAG TAC CCG AGC AGT CAG CTG GGG GAG ATG TCC CTG
     Glu Glu His Ser Gln Cys Glu Cys Arg Pro Lys Lys Lys Arg Arg Val Leu  102
259  GAA GAA CAC AGC CAA TGT GAA TGC AGA CCA AAA AAA AAA AGG AGA GTG CTG
     Stop
310  TGA AGCCAGACAGCCCCAGGATCCTCTGCCCGCCTTGCACCCAGCGCCGTCAACGCCCTGACCCCC
376  GGACCTGCCGCTGCCGCTGCAGACGCCGCCGCTTCCTCCATTGCCAAGGGCGGGGCTTAGAGCTCAA
443  CCCAGACACCTGTAGGTGCCGGAAGCCGCGAAAGTGACAAGCTGCTTTCCAGACTCCACGGGCCCGG
510  CTGCTTTTATGGCCCTGCTTCACAGGGACGAAGAGTGGAGCACAGGCAAACCTCCTCAGTCTGGGAG
577  GTCACTGCCCAGGACCTGGACCTTTTAGAGAGCTCTCTCGCCATCTTTTATCTCCCAGAGCTGCCA
644  TCTAACAATTGTCAAGGAACCTCATGTCTCACCTCAGGGGCCAGGGTACTCTCTCACTTAACCACCC
711  TGGTCAAGTGAGCATCTTCTGGCTGGCTGTCTCCCCTCACTATGAAAACCCCAAACTTCTACCAATA
778  ACGGGATTTGGGTTCTGTTATGATAACTGTGACACACACACACACTCACACTCTGATAAAAGAGAAC
845  TCTGATAAAAGAGATGGAAGACACTAAAAAAAAAAAAAAAAAA
```

(SEQ ID NOS:1 & 2)

Figure 2
Deduced amino acid sequence of 2nd reading frame of cDNA clone.

```
  1                                                              CGGGACGCC
 10  CAGTGGTGCCATGGATAGACGTTTATGCACGTGCCACATGCCAGCCCAGGGAGGTGGTGGTGCCTCT
 77  GAGCATGGAACTCATGGGCAATGTGGTCAAACAACTAGTGCCCAGCTGTGTGACTGTGCAGCGCTGT
144  GGTGGCTGCTGCCCTGACGATGGCCTGGAATGTGTGCCCACTGGGCAACACCAAGTCCGAATGCAGA
211  TCCTCATGATCCAGTACCCGAGCAGTCAGCTGGGGGAGATGTCCCTGGAAGAACACAGCCAATGTGA
                                               Lys Pro Asp Ser Pro Arg     7
278  ATG CAG ACC AAA AAA AAA AAG GAG AGT GCT GTG AAG CCA GAC AGC CCC AGG
     Ile Leu Cys Pro Pro Cys Thr Gln Arg Arg Gln Arg Pro Asp Pro Arg Thr  24
330  ATC CTC TGC CCG CCT TGC ACC CAG CGC CGT CAA CGC CCT GAC CCC GGG ACC
     Cys Arg Cys Arg Cys Arg Arg Arg Phe Leu His Cys Gln Gly Arg Gly      41
381  TGC CGC TGC CGC TGC AGA CGC CGC CGC TTC CTC CAT TGC CAA GGG CGG GGC
     Leu Glu Leu Asn Pro Asp Thr Cys Arg Cys Arg Lys Pro Arg Lys Stop     56
432  TTA GAG CTC AAC CCA GAC ACC TGT AGG TGC CGG AAG CCG CGA AAG TGA CAA
483  GCTGCTTTCCAGACTCCACGGGCCCGGCTGCTTTTATGGCCCTGCTTCACAGGGACGAAGAGTGGAG
550  CACAGGCAAACCTCCTCAGTCTGGGAGGTCACTGCCCCAGGACCTGGACCTTTTAGAGAGCTCTCTC
617  GCCATCTTTTATCTCCCAGAGCTGCCATCTAACAATTGTCAAGGAACCTCATGTCTCACCTCAGGGG
684  CCAGGGTACTCTCTCACTTAACCACCCTGGTCAAGTGAGCATCTTCTGGCTGGCTGTCTCCCCTCAC
751  TATGAAAACCCCAAACTTCTACCAATAACGGGATTTGGGTTCTGTTATGATAACTGTGACACACACA
816  CACACTCACACTCTGATAAAAGAGAACTCTGATAAAAGAGATGGAAGACACTAAAAAAAAAAAAAAA
885  AAA
```

(SEQ ID NOS:1 & 3)

Figure 3
Coding region of clones encoding murine VEGF-B$_{167}$

```
GAGCCCCCTG CTCCGTCGCC TGCTGCTTGT TGCACTGCTG CAGCTGGCTC
GCACCCAGGC CCCTGTGTCC CAGTTTGATG GCCCCAGCCA CCAGAAGAAA
GTGGTGCCAT GGATAGACGT TTATGCACGT GCCACATGCC AGCCCAGGGA
GGTGGTGGTG CCTCTGAGCA TGGAACTCAT GGGCAATGTG GTCAAACAAC
TAGTGCCCAG CTGTGTGACT GTGCAGCGCT GTGGTGGCTG CTGCCCTGAC
GATGGCCTGG AATGTGTGCC CACTGGGCAA CACCAAGTCC GAATGCAGAT
CCTCATGATC CAGTACCCGA GCAGTCAGCT GGGGGAGATG TCCCTGGAAG
AACACAGCCA ATGTGAATGC AGACCAAAAA AAAAGGAGAG TGCTGTGAAG
CCAGACAGCC CCAGGATCCT CTGCCCGCCT TGCACCCAGC GCCGTCAACG
CCCTGACCCC CGGACCTGCC GCTGCCGCTG CAGACGCCGC CGCTTCCTCC
ATTGCCAAGG GCGGGGCTTA GAGCTCAACC CAGACACCTG TAGGTGCCGG
AAGCCGCGAA AGTGA
(SEQ ID NO:4)
```

Figure 4
Deduced amino acid sequence of murine VEGF-B$_{167}$

```
MSPLLRRLLL VALLQLARTQ APVSQFDGPS HQKKVVPWID VYARATCQPR
EVVVPLSMEL MGNVVKQLVP SCVTVQRCGG CCPDDGLECV PTGQHQVRMQ
ILMIQYPSSQ LGEMSLEEHS QCECRPKKKE SAVKPDSPRI LCPPCTQRRQ
RPDPRTCRCR CRRRRFLHCQ GRGLELNPDT CRCRKPRK
(SEQ ID NO:5)
```

Figure 5
Coding sequence of clone encoding murine VEGF-B$_{174}$

```
ACCATGAGCC CCCTGCTCCG TCGCCTGCTG CTTGTTGCAC TGCTGCAGCT
GGCTCGCACC CAGGCCCCTG TGTCCCAGTT TGATGGCCCC AGCCACCAGA
AGAAAGTGGT GCCATGGATA GACGTTTATG CACGTGCCAC ATGCCAGCCC
AGGGAGGTGG TGGTGCCTCT GAGCATGGAA CTCATGGGCA ATGTGGTCAA
ACAACTAGTG CCCAGCTGTG TGACTGTGCA GCGCTGTGGT GGCTGCTGCC
CTGACGATGG CCTGGAATGT GTGCCCACTG GCAACACCA AGTCCGAATG
CAGGTACCAG GGCCTATGGG TCAGATCCTC ATGATCCAGT ACCCGAGCAG
TCAGCTGGGG GAGATGTCCC TGGAAGAACA CAGCCAATGT GAATGCAGAC
CAAAAAAAA GGAGAGTGCT GTGAAGCCAG ACAGCCCCAG GATCCTCTGC
CCGCCTTGCA CCCAGCGCCG TCAACGCCCT GACCCCGGA CCTGCCGCTG
CCGCTGCAGA CGCCGCCGCT TCCTCCATTG CCAAGGGCGG GGCTTAGAGC
TCAACCCAGA CACCTGTAGG TGCCGGAAGC CGCGAAAGTG A
(SEQ ID NO:6)
```

Figure 6
Deduced amino acid sequence of murine VEGF-B$_{174}$

MSPLLRRLLL VALLQLARTQ APVSQFDGPS HQKKVVPWID VYARATCQPR
EVVVPLSMEL MGNVVKQLVP SCVTVQRCGG CCPDDGLECV PTGQHQVRMQ
VPGPMGQILM IQYPSSQLGE MSLEEHSQCE CRPKKKESAV KPDSPRILCP
PCTQRRQRPD PRTCRCRCRR RRFLHCQGRG LELNPDTCRC RKPRK
(SEQ ID NO:7)

Figure 7
Coding region of cDNA encoding murine VEGF-B$_{112}$

ACCATGAGCC CCCTGCTCCG TCGCCTGCTG CTTGTTGCAC TGCTGCAGCT
GGCTCGCACC CAGGCCCCTG TGTCCCAGTT TGATGGCCCC AGCCACCAGA
AGAAAGTGGT GCCATGGATA GACGTTTATG CACGTGCCAC ATGCCAGCCC
AGGGAGGTGG TGGTGCCTCT GAGCATGGAA CTCATGGGCA ATGTGGTCAA
ACAACTAGTG CCCAGCTGTG TGACTGTGCA GCGCTGTGGT GGCTGCTGCC
CTGACGATGG CCTGGAATGT GTGCCCACTG GCAACACCA AGTCCGAATG
CAGATCCTCA TGATCCAGTA CCCGAGCAGT CAGCTGGGG AGATGTCCCT
GGAAGAACAC AGCCAATGTG AATGCAGACC AAAAAAAAA AGGAGAGTGC
TGTGA
(SEQ ID NO:8)

Figure 8
Deduced amino acid sequence of murine VEGF-B$_{112}$

MSPLLRRLLL VALLQLARTQ APVSQFDGPS HQKKVVPWID VYARATCQPR
EVVVPLSMEL MGNVVKQLVP SCVTVQRCGG CCPDDGLECV PTGQHQVRMQ
ILMIQYPSSQ LGEMSLEEHS QCECRPKKKR RVL
(SEQ ID NO:9)

Figure 9

Amino acid sequence alignments of mVEGF-B$_{167}$, mVEGF$_{164}$, hPlGF, mPDGF A and mPDGF B

```
mVEGF-B 167   - - - - - - - - - - - - - - - - - - - - - - - - - - - - -
mVEGF 164     - - - - - - - - - - - - - - - - - - - - - - - - - - - - -
hPlGF         - - - - - - - - - - - - - - - - - - - - - - - - - - - - -
mPDGF A       - M R T W A C L L L L G C G Y L A H A L A E E A E I P R E L
mPDGF B       M N R C W A L F L P L C C Y L R L V S A E G D P I P E E L Y mVEGF-B 167   - - - - - - - - - - - - - - - - - - - M S P L L R R L L
mVEGF 164     - - - - - - - - - - - - - - - M N F L L S W V H W T L A L
hPlGF         - - - - - - - - - - - - - - - M P V M R L F P C F L Q L
mPDGF A       I E R L A R S Q I H S I R D L Q R L L E I D S V G A E D A L
mPDGF B       E M L S D H S I R S F D D L Q R L L H R D S V D E D G A E L mVEGF-B 167   L V A L L Q L A R T Q A P V S Q F D G P S H Q K K V V P W I
mVEGF 164     L L Y L H H A K W S Q A A P - T T E G E Q K S H E V I K F M
hPlGF         L A G L A L P A V P P Q Q W A L S - A G N G S S E V E V V P
mPDGF A       E T S L R A H G S H A I N H V P E K R P V P I R R K R S I E
mPDGF B       D L N M T R A H S G V E L E S S S R G R R S L G S L A A A E mVEGF-B 167   D V Y A R A T - - C Q P R E V V V P L S M E L M G N V V K Q
mVEGF 164     D V Y Q R S Y - - C R P I E T L V D I F Q E Y P D E I E Y I
hPlGF         F Q E V W G R S Y C R A L E R L V D V V S E Y P S E V E H M
mPDGF A       E A I P A V - - - C K T R T V I Y E I P R S Q V D P T S A N
mPDGF B       P A V I A E - - - C K T R T E V F Q I S R N L I D R T N A N mVEGF-B 167   L - - V P S C V T V Q R C G G C C P D D G L E C V P T G Q H
mVEGF 164     E - - K P S C V P L M R C A G C C N D E A L E C V P T S E S
hPlGF         F - - S P S C V S L L R C T G C C G D E N L H C V P V E T A
mPDGF A       F L I W P P C V E V K R C T G C C N T S S V K C Q P S R V H
mPDGF B       F L V W P P C V E V Q R C S G C C N N R N V Q C R A S Q V Q mVEGF-B 167   Q V R M Q I L M I Q Y P S S Q - - - - L G E M S L E E H S Q
mVEGF 164     N I T M Q I M R I K P H Q S Q - - - H I G E M S F L Q H S R
hPlGF         N V T M Q L L K I R S G D R P - - - S Y V E L T F S Q H V R
mPDGF A       H R S V K V A K V E Y V R K K P K L K E V Q V R L E E H L E
mPDGF B       M R P V Q V R K I E I V R K K P I F K K A T V T L E D H L A mVEGF-B 167   C E C R P K K E S A V K P D S P R I L C P P C T Q R R Q R
mVEGF 164     C E C R P K K D R T - - K P E N H - - - C E P C S E R R K H
hPlGF         C E C R P L R E K M - - K P E - - - - R C G D A V P R R
mPDGF A       C A C A T S N L N P D H R E E E T D V R
mPDGF B       C K C E T I V T P R P V T R S P G T S R E Q R A K T P Q A R mVEGF-B 167   - - - P D P R T C R C R C R R R R F L H C Q G R G L E L N P
mVEGF 164     L F V Q D P Q T C K C S C K N T D - S R C K A R Q L E L N E
hPlGF         
mPDGF A       
mPDGF B       V T I R T V R I R P P K G K H R K F K H T H D K A A L K E mVEGF-B 167   D T C R C R K P R K
mVEGF 164     R T C R C D K P R R
hPlGF         
mPDGF A       
mPDGF B       T L G A
```

Figure 10
Coding region of a clone encoding human VEGF-B$_{167}$

ACCATGAGCC CTCTGCTCCG CCGCCTGCTG CTCGCCGCAC TCCTGCAGCT
GGCCCCCGCC CAGGCCCCTG TCTCCCAGCC TGATGCCCCT GGCCACCAGA
GGAAAGTGGT GTCATGGATA GATGTGTATA CTCGCGCTAC CTGCCAGCCC
CGGGAGGTGG TGGTGCCCTT GACTGTGGAG CTCATGGGCA CCGTGGCCAA
ACAGCTGGTG CCCAGCTGCG TGACTGTGCA GCGCTGTGGT GGCTGCTGCC
CTGACGATGG CCTGGAGTGT GTGCCCACTG GCAGCACCA AGTCCGGATG
CAGATCCTCA TGATCCGGTA CCCGAGCAGT CAGCTGGGGG AGATGTCCCT
GGAAGAACAC AGCCAGTGTG AATGCAGACC TAAAAAAAAG GACAGTGCTG
TGAAGCCAGA CAGCCCCAGG CCCCTCTGCC CACGCTGCAC CCAGCACCAC
CAGCGCCCTG ACCCCCGGAC CTGCCGCTGC CGCTGCCGAC GCCGCAGCTT
CCTCCGTTGC CAAGGGCGGG GCTTAGAGCT CAACCCAGAC ACCTGCAGGT
GCCGGAAGCT GCGAAGGTGA
(SEQ ID NO:10)

Figure 11
Deduced amino acid sequence of human VEGF-B$_{167}$

MSPLLRRLLL AALLQLAPAQ APVSQPDAPG HQRKVVSWID VYTRATCQPR
EVVVPLTVEL MGTVAKQLVP SCVTVQRCGG CCPDDGLECV PTGQHQVRMQ
ILMIRYPSSQ LGEMSLEEHS QCECRPKKKD SAVKPDSPRP LCPRCTQHHQ
RPDPRTCRCR CRRRSFLRCQ GRGLELNPDT CRCRKLRR
(SEQ ID NO:11)

Figure 12
Nucleotide sequence of coding portion of a cDNA clone encoding murine VEGF-B$_{186}$.

ATGAGCCCCC TGCTCCGTCG CCTGCTGCTT GTTGCACTGC TGCAGCTGGC
TCGCACCCAG GCCCCTGTGT CCCAGTTTGA TGGCCCCAGC CACCAGAAGA
AAGTGGTGCC ATGGATAGAC GTTTATGCAC GTGCCACATG CCAGCCCAGG
GAGGTGGTGG TGCCTCTGAG CATGGAACTC ATGGGCAATG TGGTCAAACA
ACTAGTGCCC AGCTGTGTGA CTGTGCAGCG CTGTGGTGGC TGCTGCCCTG
ACGATGGCCT GGAATGTGTG CCCACTGGGC AACACCAAGT CCGAATGCAG
ATCCTCATGA TCCAGTACCC GAGCAGTCAG CTGGGGGAGA TGTCCCTGGA
AGAACACAGC CAATGTGAAT GCAGACCAAA AAAAAGGAG AGTGCTGTGA
AGCCAGACAG GGTTGCCATA CCCCACCACC GTCCCCAGCC CCGCTCTGTT
CCGGGCTGGG ACTCTACCCC GGGAGCATCC TCCCCAGCTG ACATCATCCA
TCCCACTCCA GCCCCAGGAT CCTCTGCCCG CCTTGCACCC AGCGCCGTCA
ACGCCCTGAC CCCCGGACCT GCCGCTGCCG CTGCAGACGC CGCCGCTTCC
TCCATTGCCA AGGGCGGGGC TTAG
(SEQ ID NO:12)

Figure 13
Deduced amino acid sequence of murine VEGF-$B_{186}$.

MSPLLRRLLL VALLQLARTQ APVSQFDGPS HQKKVVPWID VYARATCQPR
EVVVPLSMEL MGNVVKQLVP SCVTVQRCGG CCPDDGLECV PTGQHQVRMQ
ILMIQYPSSQ LGEMSLEEHS QCECRPKKKE SAVKPDRVAI PHHRPQPRSV
PGWDSTPGAS SPADIIHPTP APGSSARLAP SAVNALTPGP AAAADAAAS
SIAKGGA
(SEQ ID NO:13)

Figure 14
Nucleotide sequence of coding portions of a cDNA clone H.1 encoding human VEGF-$B_{186}$.

ATGAGCCCTC TGCTCCGCCG CCTGCTGCTC GCCGCACTCC TGCAGCTGGC
CCCCGCCCAG GCCCCTGTCT CCCAGCCTGA TGCCCCTGGC CACCAGAGGA
AAGTGGTGTC ATGGATAGAT GTGTATACTC GCGCTACCTG CCAGCCCCGG
GAGGTGGTGG TGCCCTTGAC TGTGGAGCTC ATGGGCACCG TGGCCAAACA
GCTGGTGCCC AGCTGCGTGA CTGTGCAGCG CTGTGGTGGC TGCTGCCCTG
ACGATGGCCT GGAGTGTGTG CCCACTGGGC AGCACCAAGT CCGGATGCAG
ATCCTCATGA TCCGGTACCC GAGCAGTCAG CTGGGGGAGA TGTCCCTGGA
AGAACACAGC CAGTGTGAAT GCAGACCTAA AAAAAAGGAC AGTGCTGTGA
AGCCAGACAG GGCTGCCACT CCCCACCACC GTCCCCAGCC CCGTTCTGTT
CCGGGCTGGG ACTCTGCCCC CGGAGCACCC TCCCCAGCTG ACATCACCCA
TCCCACTCCA GCCCCAGGCC CCTCTGCCCA CGCTGCACCC AGCACCACCA
GCGCCCTGAC CCCCGGACCT GCCGCCGCCG CTGCCGACGC CGCAGCTTCC
TCCGTTGCCA AGGGCGGGGC TTAG
(SEQ ID NO:14)

Figure 15
Deduced amino acid sequence of human VEGF-$B_{186}$.

MSPLLRRLLL AALLQLAPAQ APVSQPDAPG HQRKVVSWID VYTRATCQPR
EVVVPLTVEL MGTVAKQLVP SCVTVQRCGG CCPDDGLECV PTGQHQVRMQ
ILMIRYPSSQ LGEMSLEEHS QCECRPKKKD SAVKPDRAAT PHHRPQPRSV
PGWDSAPGAP SPADITHPTP APGPSAHAAP STTSALTPGP AAAADAAAS
SVAKGGA
(SEQ ID NO:15)

Figure 16
Amino acid sequence alignment of VEGF-B₁₆₇ and VEGF-B₁₈₆

```
mVEGF-B186   M S P L L R R L L L V A L L Q L A R T Q A P V S Q F D G P S
hVEGF-B186   M S P L L R R L L L A A L L Q L A P A Q A P V S Q P D A P G
mVEGF-B167   M S P L L R R L L L V A L L Q L A R T Q A P V S Q F D G P S
hVEGF-B167   M S P L L R R L L L A A L L Q L A P A Q A P V S Q P D A P G mVEGF-B186   H Q K K V V P W I D V Y A R A T C Q P R E V V V P L S M E L
hVEGF-B186   H Q R K V V S W I D V Y T R A T C Q P R E V V V P L T V E L
mVEGF-B167   H Q K K V V P W I D V Y A R A T C Q P R E V V V P L S M E L
hVEGF-B167   H Q R K V V S W I D V Y T R A T C Q P R E V V V P L T V E L mVEGF-B186   M G N V V K Q L V P S C V T V Q R C G G C C P D D G L E C V
hVEGF-B186   M G T V A K Q L V P S C V T V Q R C G G C C P D D G L E C V
mVEGF-B167   M G N V V K Q L V P S C V T V Q R C G G C C P D D G L E C V
hVEGF-B167   M G T V A K Q L V P S C V T V Q R C G G C C P D D G L E C V mVEGF-B186   P T G Q H Q V R M Q I L M I Q Y P S S Q L G E M S L E E H S
hVEGF-B186   P T G Q H Q V R M Q I L M I R Y P S S Q L G E M S L E E H S
mVEGF-B167   P T G Q H Q V R M Q I L M I Q Y P S S Q L G E M S L E E H S
hVEGF-B167   P T G Q H Q V R M Q I L M I R Y P S S Q L G E M S L E E H S mVEGF-B186   Q C E C R P K K K E S A V K P D R V A I P H H R P Q P R S V
hVEGF-B186   Q C E C R P K K K D S A V K P D R A A T P H H R P Q P R S V
mVEGF-B167   Q C E C R P K K K E S A V K P D S P R I L C P P C T Q R R Q
hVEGF-B167   Q C E C R P K K K D S A V K P D S P R P L C P R C T Q H H Q mVEGF-B186   P G W D S T P G A S S P A D I I H P T P A P G S S A R L A P
hVEGF-B186   P G W D S A P G A P S P A D I T H P T P A P G P S A H A A P
mVEGF-B167   R P D P R T C R C R C R R R R F L H C Q G R G L E L N P D T
hVEGF-B167   R P D P R T C R C R C R R R S F L R C Q G R G L E L N P D T mVEGF-B186   S A V N A L T P G P A A A A A D A A A S S I A K G G A
hVEGF-B186   S T T S A L T P G P A A A A A D A A A S S V A K G G A
mVEGF-B167   C R C R K P R K
hVEGF-B167   C R C R K L R R
```

Figure 18
Hydrophilicity analysis of murine VEGF-B₁₆₇ and VEGF-B₁₈₆

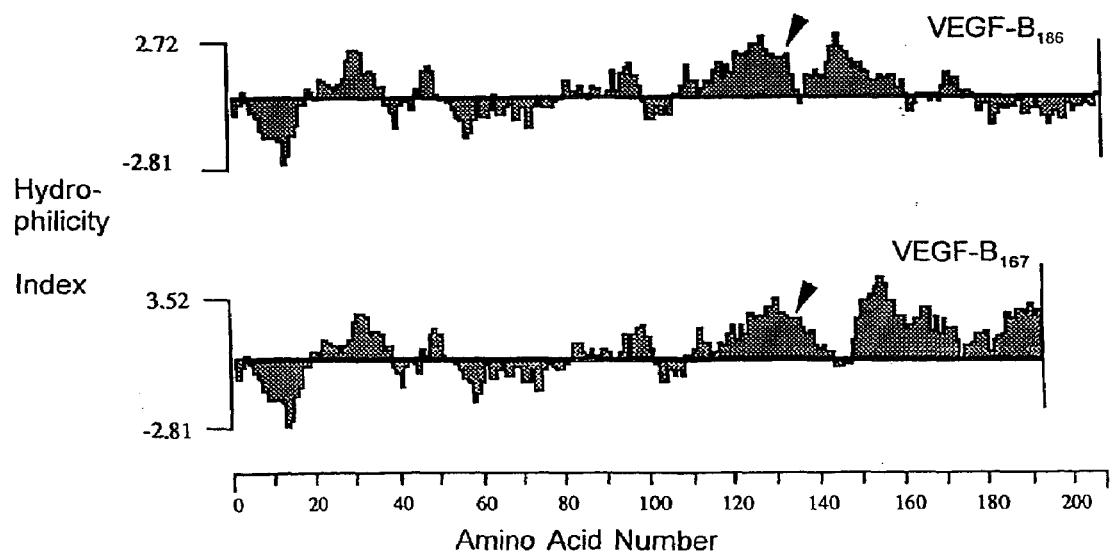

Schematic structure of murine and human genes for VEGF-B

Phylogenetic analysis of the VEGF-PDGF family of growth factors

Induction of [$^3$H]thymidine by VEGF-B

Northern blot of VEGF-B in Mouse and Human Tissues

SDS-PAGE of VEGF-B Immunoprecipitates from Transfected Cells

Derivation of VEGF-B promoter-reporter clones

Figure 25 Nucleotide Sequence of VEGF-B Promoter

```
   1 ctcgagatct gtttgttgtc ttggaacaat acggtttaga ggtgactggc
     ―――――――
      Xho I
  51 gggtgacgag aacatatgcg agttcaccta agagaaaagc tgaatgaggc
 101 aatgcctctt cctgaccata tctcttactc agataactat agaatttatt
 151 gtccagtaaa gggtatatta aaaatcata ttaaagtca tacagtgaag
                      silencer binding site 2
 201 ttgtccaggg aaatcaagac ttaacagtct cactctgaca ataatgaaca
 251 gggggattcc ctcaagatag actaggacat gaccccacac tggcaggtag
 301 tagtaccaga aaagaacgca tggaaaatct ttaccttatg cttgaggtag
 351 ggaccaggct aaagtgaagg ccagacctaa aattctatct aaaataaatc
 401 cacaatcgaa gaaaatatgt ggtgtacagg tatagaatgt ctttactgga
 451 tcattgaaat agtaagataa attcaacttt ttacattgtt ttcttttcct
 501 ccagttaggg cttgagacct tcgtctctgg agagtgactg tcaattggag
 551 ccctgctttc tgggtttctg gccagggggg ttgtggatgc ttaacatgtg
 601 cctttcacag gacacttcct taccccagca gtggccangt gtgcatccca
 651 cgaccaggcc tccctctcac ggaacatctg ttgagactag gagatgcctg
 701 gtgactgttg cctgacctgt gtcctgtgta tttctgacaa gagccactct
 751 caaagaccct ggccaggagg agagttaggt tccagtgtag gtcagctcag
 801 acagatggag gccacagaan caaacatggg aaatcacaga agtaggttta
 851 ttactcacag atccctatcc caaccaccca ggtgccctct cctccagggc
 901 caacagaggc atccttcagc aggagcgaca acggctaggg cagcggcaag
 951 ccgccaccat ccgagccaac ccaggccccg agatcgtgcc ccggggcgcc
1001 ggcccctgag gggctcacct ggatggggcc tgcatgcgtt cccgctttgc
                                             ―――
                                             Sph I
1051 ttccttccct ggacggcccg ctcccccgaa acgcgccgcc aataaagtga
1101 ttcgcagagc tcgtgtgcgg ctccctcctt aaggcccgac gccccggcc
                           SacI
1151 ccggcctcgc caagggcagc gcccggcct ccgggtagtg gcggccggcg
1201 actggggagc ccagcctcct gggcggtgcg tccccttccc cctgccgcgg
1251 cgggaggcgg gaggggtgt gtggaggagg cgggccccgc cgacggcctc
1301 gccccccac ccgccgccc cgccccgcc cacgggccc ggtggggagc
1351 gcgtgtctgg gtcacatgag ccgcctgccc gcagcccgg gccagcccc
1401 ccgccgcccc cgccgtcccc gccgccgctg cccgccgcca ccggccgccc
1451 gcccgcccgg ctcctccggc cgccttcgct gcgctgcntg cgctgcctgc
1501 acccagggct cgggagggg ccgcggagga gccgccccc gcgccggcc
...  Nco I site is about 30 bp downstream)    (SEQ ID NO:17)
```

PROCESSED VASCULAR ENDOTHELIAL GROWTH FACTOR-B POLYPEPTIDES

This application is a continuation of application Ser. No. 09/961,756, filed Sep. 25, 2001, now abandoned which is a divisional of application Ser. No. 08/851,896, filed May 6, 1997, now U.S. Pat. No. 6,331,301, and a continuation of application Ser. No. 08/609,443, filed Mar. 1, 1996, now U.S. Pat. No. 5,840,693, U.S. Ser. No. 08/851,896 is a divisional of application Ser. No. 08/469,427, filed Jun. 6, 1995, now U.S. Pat. No. 5,607,918, which is a continuation-in-part of application Ser. No. 08/397,651, filed Mar. 1, 1995, now abandoned. U.S. Ser. No. 08/609,443 is a continuation-in-part of application Ser. No. 08/569,063, filed Dec. 6, 1995, now U.S. Pat. No. 5,928,939, which is a continuation-in-part of application Ser. No. 08/469,427, the lineage of which is described above.

BACKGROUND OF THE INVENTION

Angiogenesis, or the proliferation of new capillaries from pre-existing blood vessels, is a fundamental process necessary for normal growth and development of tissues. It is a prerequisite for the development and differentiation of the vascular tree, as well as for a wide variety of fundamental physiological processes including embryogenesis, somatic growth, tissue and organ repair and regeneration, cyclical growth of the corpus luteum and endometrium, and development and differentiation of the nervous system. In the female reproductive system, angiogenesis occurs in the follicle during its development, in the corpus luteum following ovulation and in the placenta to establish and maintain pregnancy. Angiogenesis additionally occurs as part of the body's repair processes, e.g. in the healing of wounds and fractures. Angiogenesis is also a factor in tumor growth, since a tumor must continuously stimulate growth of new capillary blood vessels in order to grow.

Capillary blood vessels consist of endothelial cells and pericytes. These two cell types carry all of the genetic information to form tubes, branches and entire capillary networks. Specific angiogenic molecules can initiate this process. In view of the physiological importance of angiogenesis, much effort has been devoted to the isolation, characterization and purification of factors that can stimulate angiogenesis. A number of polypeptides which stimulate angiogenesis have been purified and characterized as to their molecular, biochemical and biological properties. For reviews of such angiogenesis regulators, see Klagsbrun et al., "Regulators of Angiogenesis", *Ann. Rev. Physiol.*, 53:217-39 (1991); and Folkman et al., "Angiogenesis," *J. Biol. Chem.*, 267:10931-934 (1992). Recent results have implicated several endothelial receptor tyrosine kinases (RTKs) in the establishment and maintenance of the vascular system.

One such growth factor, which is highly specific as a mitogen for vascular endothelial cells, is termed vascular endothelial growth factor (VEGF) See Ferrara et al., "The Vascular Endothelial Growth Factor Family of Polypeptides," *J. Cellular Biochem.*, 47:211-218 (1991); Connolly, "Vascular Permeability Factor: A Unique Regulator of Blood Vessel Function," *J. Cellular Biochem.*, 47:219-223 (1991). VEGF is a potent vasoactive protein that has been detected in media conditioned by a number of cell lines including bovine pituitary follicular cells. VEGF is a glycosylated cationic 46-48 kD dimer made up of two 24 kD subunits. It is inactivated by sulfhydryl reducing agents, resistant to acidic pH and to heating, and binds to immobilized heparin. VEGF is sometimes referred to as vascular permeability factor (VPF) because it increases fluid leakage from blood vessels following intradermal injection. It also has been called by the name vasculotropin.

Four different molecular species of VEGF have been detected. The 165 amino acid species has a molecular weight of approximately 46 kD and is the predominant molecular form found in normal cells and tissues. A less abundant, shorter form with a deletion of 44 amino acids between positions 116 and 159 ($VEGF_{121}$), a longer form with an insertion of 24 highly basic residues in position 116 ($VEGF_{189}$), and another longer form with an insertion of 41 amino acids ($VEGF_{206}$) which includes the 24 amino acid insertion found in $VEGF_{189}$, are also known. $VEGF_{121}$ and $VEGF_{165}$ are soluble proteins. $VEGF_{189}$ and $VEGF_{206}$ appear to be mostly cell-associated. All of the isoforms of VEGF are biologically active. For example, each of the species when applied intradermally is able to induce extravasation of Evans blue.

The various species of VEGF are encoded by the same gene and arise from alternative splicing of messenger RNA This conclusion is supported by Southern blot analysis of human genomic DNA, which shows that the restriction pattern is identical using either a probe for $VEGF_{165}$ or one which contains the insertion in $VEGF_{206}$. Analysis of genomic clones in the area of putative mRNA splicing also shows an intron/exon structure consistent with alternative splicing.

The different isoforms of VEGF have different chemical properties which may regulate cellular release, compartmentalization, bioavailability and possibly also modulate the signalling properties of the growth factors.

Analysis of the nucleotide sequence of the VEGF gene indicates that VEGF is a member of the platelet-derived growth factor (PDGF) family. VEGF and PlGF are ligands for two endothelial RTKs, flt-1 (VEGF receptor 1, VEGFR1) and flk-1/KDR (VEGF receptor 2, VEGFR2). The amino acid sequence of VEGF exhibits approximately 20% homology to the sequences of the A and B chains of PDGF, as well as complete conservation of the eight cysteine residues found in both mature PDGF chains. $VEGF_{165}$, $VEGF_{189}$ and $VEGF_{206}$ also contain eight additional cysteine residues within the carboxy-terminal region. The amino-terminal sequence of VEGF is preceded by 26 amino acids corresponding to a typical signal sequence. The mature protein is generated directly following signal sequence cleavage without any intervening prosequence. The existence of a potential glycosylation site at $Asn^{74}$ is consistent with other evidence that VEGF is a glycoprotein, but the polypeptide has been reported to exist in both glycosylated and deglycosylated species.

Like other cytokines, VEGF can have diverse effects that depend on the specific biological context in which it is found. VEGF and its high affinity receptors flt-1 and KDR/flk-1 are required for the formation and maintenance of the vascular system as well as for both physiological and pathological angiogenesis. VEGF is a potent endothelial cell mitogen and directly contributes to induction of angiogenesis in vivo by promoting endothelial cell growth during normal embryonic development, wound healing, and tissue regeneration and reorganization. VEGF is also involved in pathological processes such as growth and metastasis of solid tumors and ischemia-induced retinal disorders. A most striking property of VEGF is its specificity. It is mitogenic in vitro at 1 ng/ml for capillary and human umbilical vein endothelial cells, but not for adrenal cortex cells, corneal or lens epithelial cells, vascular smooth muscle cells, corneal endothelial cells, granulosa cells, keratinocytes, BHK-21 fibroblasts, 3T3 cells, rat embryo fibroblasts, human placental fibroblasts and human sarcoma cells. The target cell specificity of VEGF is thus restricted to vascular endothelial cells. VEGF can trigger the entire sequence of events leading to angiogenesis and stimulates angiogenesis in vivo in the cornea and in a healing bone graft model. It is able to stimulate the proliferation of endothelial cells isolated from both small and large vessels. Expression of VEGF mRNA is temporally and spatially related to the physiological proliferation of capillary blood vessels in the ovarian corpus luteum or in the developing brain. VEGF expression is triggered by hypoxia so that endothelial cell proliferation and angiogenesis appear to be especially stimulated in ischemic areas. VEGF is also a potent chemoattractant for monocytes. In addition, VEGF induces plasminogen activator and plasminogen activator inhibitor in endothelial cells.

Tumor cells release angiogenic molecules such as VEGF, and monoclonal antibodies to VEGF have been shown to inhibit the growth of certain types of tumor such as rhabdomyosarcoma. See Kim et al., "Inhibition of Vascular Endothelial Growth Factor-Induced Angiogenesis Suppresses Tumor Growth in vivo," *Nature*, 362:841-844 (1993). This suggests that blocking VEGF action is of potential therapeutic significance in treating tumors in general, and highly-vascularized, aggressive tumors in particular.

SUMMARY OF THE INVENTION

It is an object of the invention to provide a new growth factor having the property of promoting proliferation of endothelial cells.

Another object of the invention is to provide isolated DNA sequences which encode a new growth factor which promotes proliferation of endothelial cells.

It is also an object of the invention to provide new products which may be useful in diagnostic and/or therapeutic applications.

These and other objects are achieved in accordance with the present invention by providing an isolated DNA which codes for a protein exhibiting the following characteristic amino acid sequence (SEQ ID NO:16):

Pro-Xaa-Cys-Val-Xaa-Xaa-Xaa-Arg-Cys-Xaa-Gly-Cys-Cys and having the property of promoting proliferation of endothelial cells or mesodermal cells, the DNA being selected from the group consisting of the DNA of FIGS. 1 and 2 (SEQ ID NO:1), the DNA of FIG. 3 (SEQ ID NO:4), the DNA of FIG. 5 (SEQ ID NO:6); the DNA of FIG. 7 (SEQ ID NO:8), the DNA of FIG. 10 (SEQ ID NO:10), the DNA of FIG. 12 (SEQ ID NO:12), the DNA of FIG. 14 (SEQ ID NO:14), and DNA's which hybridize under stringent conditions with at least one of the foregoing DNA sequences.

In accordance with further aspects of the invention, the objects are also achieved by providing a protein exhibiting the following characteristic amino acid sequence Pro-Xaa-Cys-Val-Xaa-Xaa-Xaa-Arg-Cys-Xaa-Gly-Cys-Cys (SEQ ID NO:16) and having the property of promoting proliferation of endothelial cells or mesodermal cells, which protein comprises a sequence of amino acids substantially corresponding to an amino acid sequence selected from the group consisting of the amino acid sequence of FIG. 1 (SEQ ID NO:2), the amino acid sequence of FIG. 2 (SEQ ID NO:3), the amino acid sequence of FIG. 4 (SEQ ID NO:5), the amino acid sequence of FIG. 6 (SEQ ID NO:7), the amino acid sequence of FIG. 8 (SEQ ID NO:9), the amino acid sequenc of FIG. 11 (SEQ ID NO:11), the amino acid sequence of FIG. 13 (SEQ ID NO:13), and the amino acid sequence of FIG. 15 (SEQ ID NO:15).

In further aspects of the invention, the objects are achieved by providing pharmaceutical preparations which comprise such proteins; and by providing antibodies which react with or recognize such proteins.

The novel growth factor of the present invention, referred to hereinafter as vascular endothelial growth factor B or VEGF-B, has close structural similarities to VEGF and to placenta growth factor (PlGF). All of the VEGF-B forms contain the characteristic amino acid sequence Pro-Xaa-Cys-Val-Xaa-Xaa-Xaa-Arg-Cys-Xaa-Gly-Cys-Cys (SEQ ID NO:16) (wherein Xaa represents a variable residue), which is an earmark of the PDGF/VEGF family of growth factors. This characteristic amino acid sequence can be found at amino acids 70 to 82 in FIGS. 4, 6, 8, 11, 13 and 15.

Clinical applications of the invention include diagnostic applications, acceleration of angiogenesis in wound healing, and inhibition of angiogenesis. Quantitation of VEGF-B in cancer biopsy specimens may be useful as an indicator of future metastatic risk. Topical application of VEGF-B preparations to chronic wounds may accelerate angiogenesis and wound healing. VEGF-B may be used in a manner analogous to VEGF.

According to yet further aspects of the invention, the objects are achieved by providing diagnostic/prognostic means typically in the form of test kits. For example, in one embodiment of the invention there is provided a diagnostic/prognostic test kit comprising antibodies to the new growth factor of the invention and means for detecting, and more preferably evaluating, binding between the antibodies and the new growth factor of the invention. In one preferred embodiment of the diagnostic/prognostic means according to the invention, either the antibody or the new growth factor is labelled, and either the antibody or the growth factor is substrate-bound, such that the growth factor-antibody interaction can be established by determining the amount of label attached to the substrate following binding between the antibody and the growth factor. In a particularly preferred embodiment of the invention, the diagnostic/prognostic means may be provided as a conventional ELISA kit.

In another alternative embodiment, the diagnostic/prognostic means may comprise PCR means for establishing the genomic sequence structure of a VEGF-B gene of a test individual and comparing this sequence structure with that disclosed in this application in order to detect any abnormalities, with a view to establishing whether any aberrations in VEGF-B expression are related to a given disease condition.

A yet further aspect of the invention concerns an antibody which recognizes VEGF-B and which is suitably labelled.

Another aspect of the invention concerns the provision of a pharmaceutical composition comprising either VEGF-B protein or antibodies thereto. Compositions which comprise VEGF-B protein may optionally further comprise either VEGF or heparin or both.

According to an additional aspect of the invention the manufacture of a medicament is provided which comprises VEGF-B protein and heparin for treating conditions characterized by lack of, or reduction in, angiogenesis.

In another aspect, the invention relates to a protein dimer comprising VEGF-B protein, particularly a disulfide-linked dimer. The protein dimers of the invention include both homodimers of VEGF-B protein and heterodimers of VEGF-B and VEGF.

According to a yet further aspect of the invention there is provided a method for facilitating release of VEGF and/or VEGF-B from a cell comprising exposing a cell which expresses either or both of the aforementioned growth factors to heparin.

Another aspect of the invention involves providing a vector comprising an anti-sense nucleotide sequence which is complementary to at least a part of the DNA sequences disclosed herein which encode the new growth factor of the invention which promotes proliferation of endothelial cells. According to a yet further aspect of the invention such a vector comprising an anti-sense sequence may be used to inhibit, or at least mitigate, VEGF-B expression. The use of a vector of this type to inhibit VEGF-B expression is favored in instances where VEGF-B expression is associated with a disease such as in instances where tumors produce VEGF-B in order to provide for angiogenesis. Transformation of such tumor cells with a vector containing an anti-sense nucleotide sequence would suppress or retard angiogenesis and so would inhibit or retard growth of the tumor.

BRIEF DESCRIPTION OF THE DRAWINGS

FIG. 1 shows the nucleotide sequence of the (partial) cDNA clone of VEGF-B (SEQ ID NO:1) and the amino acid sequence of the protein segment (SEQ ID NO:2) coded by the first reading frame of the cDNA;

FIG. 2 repeats the nucleotide sequence of the (partial) cDNA clone of VEGF-B (SEQ ID NO:1) and the amino acid sequence of the protein segment (SEQ ID NO:3) coded by the second reading frame of the cDNA;

FIG. 3 shows the nucleotide sequence of the coding region of a full length cDNA clone of murine VEGF-$B_{167}$ (SEQ ID NO:4);

FIG. 4 shows the amino acid sequence of murine VEGF-$B_{167}$ (SEQ ID NO:5);

FIG. 5 shows the nucleotide sequence of the coding region of a cDNA clone of VEGF-$B_{174}$ (SEQ ID NO:6);

FIG. 6 shows the amino acid sequence of VEGF-$B_{174}$ (SEQ ID NO:7);

FIG. 7 shows the nucleotide sequence of a cDNA clone of VEGF-$B_{112}$ (SEQ ID NO:8);

FIG. 8 shows the amino acid sequence of VEGF-$B_{112}$ (SEQ ID NO:9);

FIG. 9 shows a comparison of the amino acid sequences of mVEGF-$B_{167}$ (SEQ ID NO: 5), mVEGF$_{164}$ (SEQ ID NO: 58), hPlGF (SEQ ID NO: 59), mPDGF A (SEQ ID NO: 60), and mPDGF B (SEQ ID NO: 61);

FIG. 10 shows the nucleotide sequence of a clone of human VEGF-$B_{167}$ (SEQ ID NO:10);

FIG. 11 shows the amino acid sequence of human VEGF-$B_{167}$ (SEQ ID NO:11); and FIG. 12 shows the nucleotide sequence of murine VEGF-$B_{186}$ (SEQ ID NO:12);

FIG. 13 shows the amino acid sequence of murine VEGF-$B_{186}$ (SEQ ID NO:13);

FIG. 14 shows the nucleotide sequence of human VEGF-$B_{186}$ (SEQ ID NO:14);

FIG. 15 shows the amino acid sequence of human VEGF-$B_{186}$ (SEQ ID NO:15);

FIG. 16 shows an amino acid sequence comparison of murine and human VEGF-$B_{167}$ and VEGF-$B_{186}$ isoforms (SEQ ID NOS: 5, 11, 13 & 15).

FIG. 18 shows a hydrophilicity analysis of murine VEGF-$B_{167}$ and VEGF-$B_{186}$ isoforms;

FIG. 25 shows the nucleotide sequence of a 1.55 kb human VEGF-B promoter fragment (SEQ ID NO:17).

DETAILED DESCRIPTION OF PREFERRED EMBODIMENTS

Figure 17:
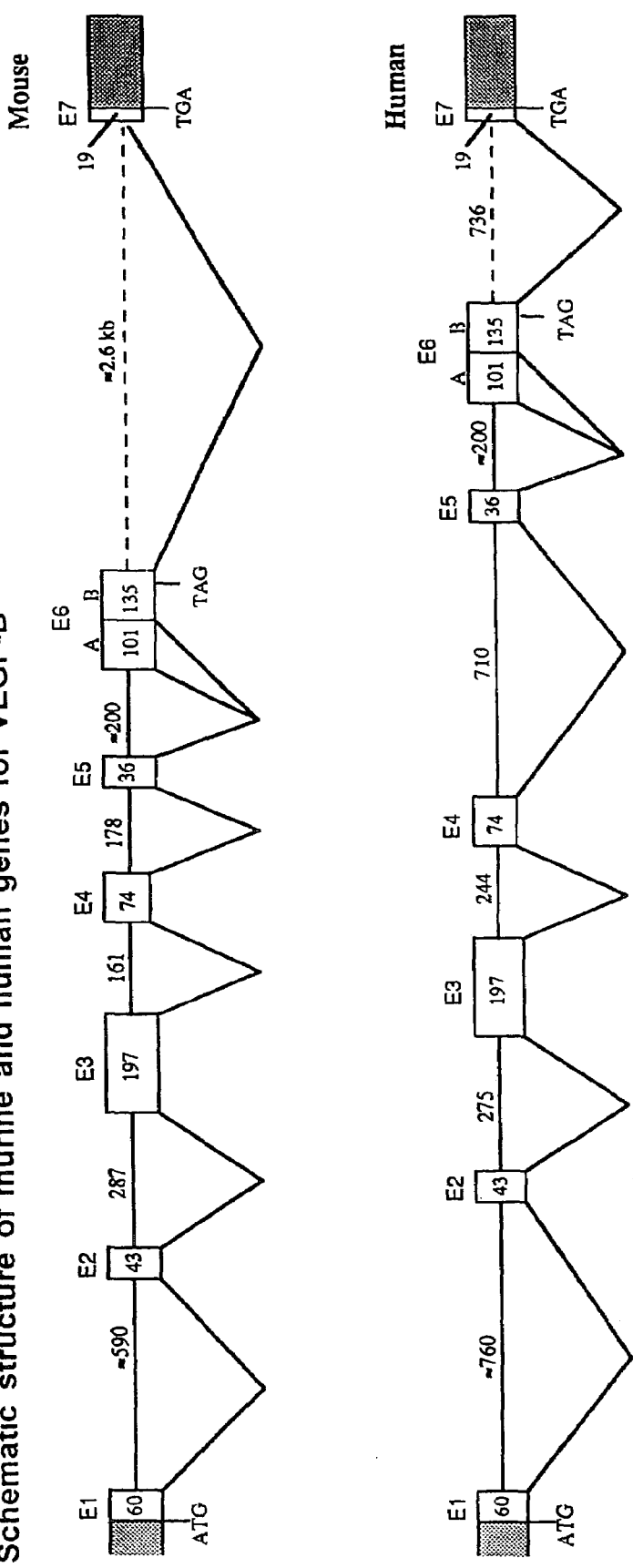
FIG. 17 shows the schematic structure of mouse and human genes for VEGF-B.

The present invention thus is directed to new vascular endothelial growth factors, hereinafter referred to as VEGF-B growth factors, which share the angiogenic and other properties of VEGF, but which are distributed and expressed in tissues differently from VEGF.

VEGF-B growth factors are members of the family of platelet derived growth factors and are a growth factors which promote mitosis and proliferation of vascular endothelial cells and/or mesodermal cells. They are produced by expression of DNA sequences which correspond to, or which are hybridizable under stringent conditions with, any one of the DNA sequences depicted in FIGS. 1 and 2 (SEQ ID NO:1), FIG. 3 (SEQ ID NO:4), FIG. 5 (SEQ ID NO:6), FIG. 7 (SEQ ID NO:8), FIG. 10 (SEQ ID NO:10), FIG. 12 (SEQ ID NO:12) or FIG. 14 (SEQ ID NO:14). It is intended to include within the scope of the invention all angiogenic proteins encoded by DNA sequences which hybridize under stringent conditions to any one of the foregoing DNA sequences. Suitable hybridization conditions include, for example, 50% formamide, 5×SSPE buffer, 5× Denhardts solution, 0.5% SDS and 100 µg/ml of salmon sperm DNA at 42° C. overnight, followed by washing 2×30 minutes in 2×SSC at 55° C.

The invention is also directed to an isolated and/or purified DNA which corresponds to, or which hybridizes under stringent conditions with, any one of the foregoing DNA sequences.

In a further aspect, the invention is directed to antibodies of VEGF-B growth factors, and particularly to monoclonal antibodies.

VEGF-B proteins are believed to interact with protein tyrosine kinase growth factor receptors. Details of such receptors are known in the art [See e.g. Wilks, A. F., "Protein Tyrosine Kinase Growth Factor Receptors and Their Ligands in Development, Differentiation, and Cancer," *Adv. Cancer Res.*, 60:43-73 (1993)].

Various adult mouse tissues were tested for expression of transcripts corresponding to VEGF-B by Northern blotting. The size of the mRNA was 1.3-1.4 kb. A mouse multiple tissue Northern blot (MTN, Clontech) was probed with the ≈0.9 kb SalI/NotI fragment derived from the pPC67 yeast expression vectors described above. The probe was labelled with $^{32}$P-dCTP using random priming (specific activity $10^8$-$10^9$ cpm/μg of DNA). The blot was hybridized overnight at 42° C. using 50% formamide, 5×SSPE buffer, 2% SDS, 10× Denhardts solution, 100 μg/ml salmon sperm DNA and $1\times10^6$ cpm of the labelled probe/ml. The blot was washed at room temperature for 2×30 min in 2×SSC containing 0.05% SDS and then for 2×20 min at 52° C. in 0.1×SSC containing 0.1% SDS. The blot was then exposed at −70° C. for three days using intensifying screens. Kodak XAR film was used. The relative expression levels as determined by visual examinations of the film are listed in the following table:

TABLE 1

Distribution of VEGF-B Transcripts in the Adult Mouse

| Tissue | Relative Expression Level |
|---|---|
| Heart | +++++ |
| Brain | +++ |
| Spleen | (+) |
| Lung | ++ |
| Liver | + |
| Skeletal Muscle | ++++ |
| Kidney | +++ |
| Testis | (+) |

+++++ = very strong expression;
++++ = strong expression;
+++ = moderate expression;
++ = rather weak expression;
+ = weak expression;
(+) = very weak expression.

A human multiple tissue Northern blot (MNT) from Clontech was probed using the murine partial cDNA to determine relative VEGF-B expression levels in various human tissues. The size of the transcript was 1.3-1.4 kb. The conditions were identical to those used for the mouse Northern blot described above. The relative VEGF-B transcript levels for the human Northern blot are listed in the following Table 2. For comparison purposes, Table 2 also lists relative expression level data from the literature for VEGF in various mammalian systems.

TABLE 2

| | Relative Expression Levels | | | |
|---|---|---|---|---|
| | VEGF-B (Northern blot) | VEGF (from literature) | | |
| Tissues | human | human | murine | guinea pig |
| heart | +++++ | ++ | +++ | +++ |
| brain | + | | + | + |

TABLE 2-continued

| | Relative Expression Levels | | | |
|---|---|---|---|---|
| | VEGF-B (Northern blot) | VEGF (from literature) | | |
| Tissues | human | human | murine | guinea pig |
| placenta | + | | | |
| lung | + | ++++ | | ++ |
| liver | (+) | ++ | (+) | + |
| skeletal muscle | ++++ | | +++ | + |
| kidney | + | ++ | + | ++ |
| pancreas | +++ | | | |
| spleen | ++ | | − | + |
| thymus | + | | − | |
| prostate | +++ | | | |
| testis | ++ | | | (+) |
| ovary | +++ | | | − |
| small intestine | ++ | | | |
| colon | +++ | | | |
| peripheral blood leucocytes | + | | | |

From a comparison of Table 1 and Table 2 it can be seen that mouse and human tissue expression levels of VEGF-B transcripts are relatively similar with the highest expression levels being found in heart and skeletal muscle. Significant differences may be seen in brain and kidney tissue. It should also be noted that tissues containing a large proportion of both muscular and epithelial cells, such as prostate, pancreas and colon from which some of the most common human tumors originate, express relatively high levels of VEGF-B.

A comparison of the relative expression levels of VEGF and VEGF-B in human tissues shows some striking differences. VEGF is expressed rather weakly by human heart tissue, but VEGF-B is very strongly expressed by the same tissue. On the other hand, VEGF is strongly expressed by human lung tissue, but VEGF-B is only weakly expressed by human lung tissue. In a similar vein, human liver tissue expresses VEGF at a moderate level, but VEGF-B is expressed only very weakly. These data evidence that despite their general similarities, the actions of VEGF and VEGF-B are not completely identical.

The expression of VEGF-B transcripts was further analyzed in mouse and human tissues by Northern blotting and compared with the expression of VEGF transcripts. Mouse and human multiple tissue Northern (MTN) blots (Clontech) were hybridized with a $^{32}$P-labelled mouse VEGF-B probe (≈0.9 kb SalI/NotI insert of the clone pcif 2). VEGF expression was analyzed with $^{32}$P-labelled VEGF$_{165}$ cDNA as the probe. The hybridizations were carried out at 42° C. in 50% deionized formamide, 5×SSC pH 7.0, 1% SDS, 5× Denhardt's solution and 100 μg/ml of denatured salmon sperm DNA. The filters were washed 2×30 min at 52° C. in 2×SSC containing 0.5% SDS and exposed to Kodak XAR film for 2-5 days at −70° C. using intensifying screens. In situ hybridization analysis of adult mouse tissues from CBA mice and of embryos derived from matings of CBA and NMRI mice were carried out essentially as previously described by Korhonen et al., *Blood,* 80, 2548-55 (1992). The RNA probes (a 383 bp antisense probe and a 169 bp sense probe) were generated from a linearized plasmid containing a 440 bp Sal I/Sac I fragment derived from the pcif 2 cDNA clone. Radiolabelled RNA was synthesized using T7 and SP6 RNA polymerases and [$^{35}$S]UTP (Amersham Inc.). Alkaline hydrolysis of the probes was omitted. Hematoxylin was used for counterstaining. Control hybridizations with sense strand and RNAse A-treated sections did not give signals above background.

In mouse tissues the most abundant expression of the 1.4 kb VEGF-B transcript was detected in heart, brain, skeletal muscle, and kidney. The major 3.7 kb VEGF transcript was is expressed in heart, brain, lung, skeletal muscle and kidney. In human tissues, the most abundant expression of the 1.4 kb VEGF-B transcript and the major 3.7 and 4.5 kb VEGF transcripts were detected in heart, skeletal muscle, pancreas and prostate. Thus, although clear quantitative differences exist, it appears that VEGF-B and VEGF are coexpressed in many human and mouse tissues.

The expression of VEGF-B transcripts was further examined by in situ hybridization in sections from adult mouse heart and skeletal muscle, and from the early (E 10) mouse embryo. In the adult heart, VEGF-B transcripts are prominently expressed in the myocardium, while-no specific signal is detected in arterial smooth muscle. In adult striated muscle, VEGF-B transcripts are expressed by some of the myofibers whereas others seem to lack the transcript. In the E 10 mouse embryo, VEGF-B transcripts are detected mainly in the developing heart. The myocardium of the adult mouse heart has a prominent signal. In striated muscle, VEGF-B expression is seen in subpopulations of myofibers.

Strong signals were also obtained in the developing heart of the E10 mouse embryo. Other embryonic structures expressed lower or undetectable levels of transcripts for VEGF-B.

Figure 21:
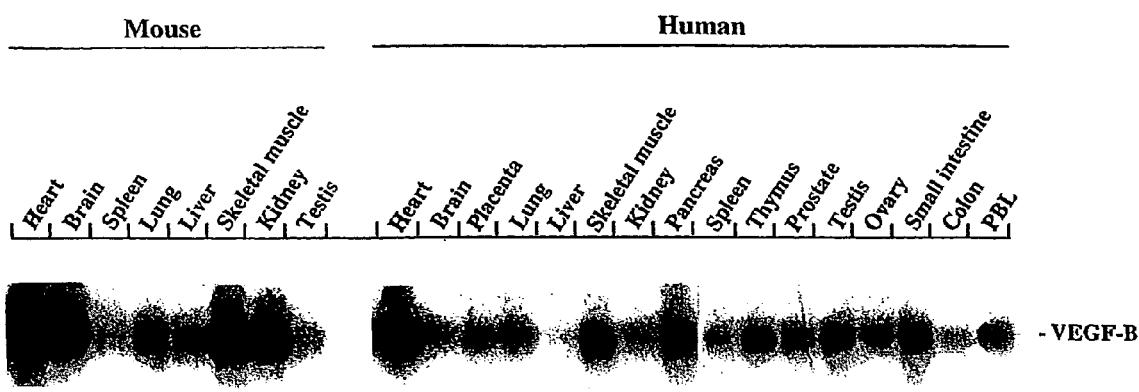
FIG. 21 is a Northern blot analysis of the expression of VEGF-$B_{186}$ transcripts in several mouse and human tissues.

Taken together, these tests indicate that VEGF-B transcrips are expressed primarily in muscular tissues. VEGF-B is particularly abundant in heart and skeletal muscle and is co-expressed with VEGF in these and other tissues. In transfected cells, VEGF-B forms cell surface associated, disulfide-linked homodimers and heterodimers with VEGF when coexpressed. A Northern blot analysis of the expression of VEGF-$B_{186}$ transcripts in several mouse and human tissues using a VEGF-$B_{186}$ isoform specific probe is shown in FIG. 21.

The chromosomal location of the VEGF-B gene was assessed by Southern blotting and polymerase chain reaction analysis of somatic cell hybrids and fluorescense in situ hybridization (FISH) of metaphase chromosomes. The VEGF-B gene was found on chromosome 11q13, proximal of the cyclin D1 gene. It is interesting that although the cyclin D1 gene is amplified in a number of human carcinomas, the VEGF-B gene was not amplified in several mammary carcinoma cell lines which contained amplified cyclin D1. Nevertheless, mutations in the VEGF-B gene may be related to vascular malformations and/or cardiovascular diseases.

Unless otherwise indicated, the following Examples used standard molecular biology techniques and procedures as disclosed in Ausubel et al. (eds.), *Current Protocols in Molecular Biology*, John Wiley & Sons, New York (1992).

EXAMPLE 1

Partial cDNA Clone with Two Reading Frames

A partial cDNA clone encoding murine VEGF-B was identified as follows. A cDNA library (E 14.5) derived from poly A+ mRNA isolated from 14.5 day old mouse embryos [Chevray P. and Nathans D., "Protein interaction cloning in yeast: Identification of mammalian proteins that react with the leucine zipper of Jun," *Proc. Natl. Acad. Sci. USA,* 89:5789-93 (1992)] was screened for cellular proteins which potentially might interact with cellular retinoic acid-binding protein type 1 (CRABP-I) using a yeast two-hybrid interaction trap screening technique as described by Gyuris J., Golemis E., Chertkov H. and Brent R., "Cdi1, a Human G1 and S Phase Protein Phosphatase That Associates with Cdk2," *Cell,* 75:791-803 (1993). This screening technique involves a fusion protein that contains a binding domain and that is known to be transcriptionally inert (the "bait"); reporter genes that have no basal transcription and that are bound by the bait; and an expression library which encodes proteins expressed as chimeras and whose amino termini contain an activation domain and other useful moieties (the "prey"). The screened library was a 14.5 day mouse embryo plasmid library in the yeast expression vector pPC67 obtained from Dr. Pierre Chevray of the Johns Hopkins University, School of Medicine, 725 North Wolfe St., Baltimore, Md. 21205. A positive cDNA clone (pcif-2) was recovered from the screening. The positive clone was sequenced using well known, conventional techniques and found to encode a protein highly homologous to VEGF and the other members of the PDGF family of growth factors. The ≈0.9 kb SalI/NotI insert in the plasmid pPC67 was cloned into pBluescript and fully sequenced using T7 and T3 vector primers together with internal primers. The plasmid pBluescript is commercially available from Stratagene Inc., LaJolla, Calif. The cDNA insert was found to be 886 base pairs long and to encode two polypeptides in different reading frames which were homologous to the N-terminal end and the C-terminal end, respectively, of VEGF. This novel growth factor is referred to hereinafter as VEGF-B. The clone is partial and lacks several amino acids in the amino terminal region and the entire signal sequence.

FIG. 1 shows the nucleotide sequence (SEQ ID NO:1) of this partial cDNA clone of VEGF-B and the amino acid sequence (SEQ ID NO:2) encoded in the first reading frame thereof. The DNA sequence of FIG. 1 was obtained by conventional sequencing of a clone (pcif-2) in the yeast expression vector pPC67. The clone comprised 886 base pairs and encoded a part of murine VEGF-B.

The isolated cDNA sequence will hybridize with the mammalian genomic DNA, e.g. either murine or human, which contains the VEGF-B gene. In addition to the coding sequence, the genomic DNA will contain one or more promoter sequence(s) which give and direct expression of VEGF-B in one or more specific tissues. Thus the coding sequence of VEGF-B may be linked to muscle-specific promoter elements which in turn are specific to certain types of muscle fibers.

The nucleotide sequence is translated in two different reading frames into two different amino acid sequences. There is a stop codon (TGA) within the coding sequence at base pairs 309-311. Thus, VEGF-B comes in several splicing variants. The 5'end of the cloned cDNA sequence encodes an 102 amino acid long protein with significant homology to the N-terminal domains of VEGF, PlGF and PDGF A and B. In particular, a number of cysteine residues are perfectly conserved within this group of proteins. In addition to the nucleotide sequence (SEQ ID NO:1), FIG. 1 further depicts the deduced amino acid sequence (SEQ ID NO:2) of this first protein.

Translation of the C-terminal end of the cDNA (base pairs 308-475) in a different reading frame results in a protein which is highly homologous to the C-terminal part of VEGF$_{165}$, VEGF$_{189}$ and VEGF$_{206}$. FIG. 2 again shows the nucleotide sequence (SEQ ID NO:1) of FIG. 1, but this time includes the deduced amino acid sequece (SEQ ID NO:3) of the second protein, which is encoded in the second reading frame and is 54 amino acids long. It thus appears that the VEGF-B gene encodes different proteins using alternative splicing of the primary transcript. The last part of the clone, encoding the second peptide might be expressed as a functional protein in other spliced variants of VEGF-B.

The aforedescribed proteins may exist in combined association with an additional N-terminal sequence of approximately five (5) to ten (10) amino acids, as well as a further leader sequence of approximately twenty-one (21) to twenty-eight (28) amino acids. Inasmuch such combined amino acid sequences exhibit the property of promoting the proliferation of endothelial cells and the DNA sequences which code for such combined peptide sequences will hybridize under stringent conditions with the DNA sequence of FIGS. 1 and 2, such amino acid sequences and the DNA which codes for them are expressly contemplated to be within the scope of the present invention.

EXAMPLE 2

Cloning of Full Length cDNA's for Mouse VEGF-B

Using the approximately 0.9 kb SalI/NotI cDNA insert of the previously identified cDNA clone of Example 1 as a probe, an adult mouse heart lambda ZAP-II cDNA library obtained from Stratagene Inc., of La Jolla, Calif. was screened using standard techniques. The library was titrated and plated as recommended and filters were prepared. Following prehybridization at 42° C. in 50% formamide, 5×SSPE, 5× Denharts solution, 1% SDS and 100 ug of salmon sperm DNA/ml, the filters were hybridized at the same temperature and in the same solution containing the denatured radiolabelled probe using $10^6$ cpm/ml of hybridization solution. The probe was labelled using a random priming kit (Amersham). After 16 hours the filters were washed in 2×SSC containing 0.5% SDS for 2×30 mins at 52° C. The filters were exposed overnight using intensifying screens at −70° C. Positive clones were rescreened two times until all plaques on a plate were positive. The inserts from several positive clones were subcloned into the plasmid pBluescript SK+ by in vivo excision as recommended by the supplier.

Several clones were mapped by restriction enzyme analysis and were found to fall into two distinct groups characterized by the length of a Spe1/BamH1 restriction fragment. The first of these groups comprised three of the restriction mapped clones which each had a 240 bp Spe1/BamH1 restriction fragment. The other group comprised a clone which had a 340 bp Spe1/BamH1 fragment. Analysis of this fragment is described in Example 5.

The three clones which exhibited the 240 bp Spe1/BamH1 restriction fragment were fully or partially sequenced (Sequenase 2.0, U.S. Biochemicals), and the characteristics of the clones are summarized as follows:

Nucleotide sequence analyses revealed that two of the cDNA clones were substantially identical, although they differed in length, and one had a mutation. One of the clones was full length and contained an open reading frame encoding 188 amino acid residues in which the first 21 amino acids are a clevable signal sequence. The other of the two substantially identical clones terminated at the G of the start initiation codon. It could be inferred by sequence analysis of additional clones that the sequence preceeding the G reads ACCAT. Both of the clones were found to have the same coding region nucleotide sequence, which is depicted in FIG. 3 (SEQ ID NO:4). The figure omits the initial thymine and adenine of the start codon (TAG) which were not present in the isolated clones. The deduced amino acid sequence of the open reading frame of the coding region of both of these two cDNA clones is shown in FIG. 4 (SEQ ID NO:5). The resulting protein encoded by this sequence is referred to hereinafter as VEGF-B$_{167}$. In each of the protein names used herein, the subscript number refers to the number of amino acids in the mature protein without the signal sequence.

As would be expected, a comparison of the amino acid sequence encoded by these two clones with the partial amino acid sequence deduced from cDNA clone of Example 1 showed a striking similarity. However, the two open reading frames in the clone of Example 1, each of which encoded an amino acid sequence homologous to a different portion of VEGF, are both present in the same reading frame in each of these two clones according to Example 2. The frame shift in the clone of Example 1 is caused by an insertion of two extra adenine units which displace the C-terminal part of the clone of Example 1 out of frame. The reason for this is not presently understood, but may be due to a cloning artifact.

The coding part of the third clone had a nucleotide sequence identical to those of the preceding two clones except for a 21 bp insertion. FIG. 5 shows the nucleotide sequence of this third clone (SEQ ID NO:6). To facilitate identification, the 21 extra bases are underlined in the Figure. This insertion gives rise to 7 additional amino acid residues in the mature protein. Thus the resulting protein encoded by this longer cDNA is termed VEGF-B$_{174}$. The amino acid sequence of the protein encoded by the cDNA of FIG. 5 is depicted in FIG. 6 (SEQ ID NO:7). The seven additional amino acids also are underlined in the figure for ease of identification. The additional amino acids are inserted into the sequence in a splice site, and sequencing of mouse genomic DNA clones indicates that these additional amino acids are the result of true alternative splicing. Furthermore, based on what is known about the receptor binding site locations of PDGF, the insertion occurs in a position in the protein which is probably part of a receptor binding site. The insertion is thus likely to affect receptor binding and could be of functional importance in influencing antagonist and/or different receptor specificity.

EXAMPLE 3

Hybrid cDNA Clone

As previously pointed out this original cDNA clone of Example 1 was not full length and may contain an artifact. However, if the extreme 5' nucleotide sequence of the clones which encode VEGF-B$_{167}$ and/or VEGF-B$_{174}$ is added, the open reading frame encodes a protein of 133 amino acids, yielding a mature protein which is 112 amino acids long and hence is named VEGF-B$_{112}$. The hybrid cDNA sequence encoding VEGF-B$_{112}$ (SEQ ID NO:8) is shown in FIG. 7, and the amino acid sequence of the corresponding protein (SEQ ID NO:9) is illustrated in FIG. 8.

FIG. 9 shows a multiple amino acid sequence alignment for comparison purposes of the 167 amino acid variant of mouse Vascular Endothelial Growth Factor B (mVEGF-B$_{167}$), mouse Vascular Endothelial Growth Factor (mVEGF$_{164}$), human Placenta Growth Factor (hPlGF), mouse Platelet Derived Growth Factor A (mPDGF A), and mouse Platelet Derived Growth Factor B (mPDGF B). Amino acid residues identical to mouse VEGF-B$_{167}$ are boxed. The homologous relationship of the sequences is apparent, and the figure clearly demonstrates the conserved structure of the growth factors belonging to the PDGF/ VEGF family of growth factors, and that VEGF-B is a structural homolog of the other growth factors of this group. Pairwise comparisons of the amino acid sequences show that mouse VEGF-B is approximately 43% identical to mouse VEGF$_{164}$, approximately 30% identical to human PlGF, and approximately 20% identical to mouse PDGF A and B. The conserved cysteine residues are particularly noteworthy. It can be seen that the first eight cysteine residues in the N-terminal domains (i.e. the PDGF-like domains) of the five growth factors are shared by all members of this family, and it is thus evident that the eight cysteine residues, which are involved in intramolecular and intermolecular disulfide bonding, are invariant among these growth factors. Furthermore, the C-terminal domains of mouse VEGF-B$_{167}$ and VEGF$_{164}$ also display a significant similarity with eight additional conserved cysteine residues and several stretches of basic amino acids.

EXAMPLE 4

Cloning of Human VEGF-B cDNA $10^6$ λ-clones of human fibrosarcoma cDNA library HT1080 in λgt11 (Clontech) were screened with the ≈0.9 kb insert of the mouse VEGF-B clone pcif 2 according to standard procedures. Among several positive clones, one, termed H.1 was analyzed more carefully and its nucleotide sequence was determined. The nucleotide sequence indicated that a 207 amino acid isoform of human VEGF-B was encoded. Analysis of this isoform is described subsequently in Example 6. Based on the H.1 sequence two oligonucleotides were designed that would amplify the whole coding region of putative human cDNA corresponding to mouse VEGF-B$_{167}$ isoform:

```
5'-CACCATGAGCCCTCTGCTCC-3'    (SEQ ID NO:18)
(forward)

5'-GCCATGTGTCACCTTCGCAG-3'    (SEQ ID NO:19)
(reverse)
```

These oligonucleotides were used to amplify by polymerase chain reaction (PCR) the whole coding region of human VEGF-B from oligo-dT primed human erythroleukemia cell (HEL) RNA. The amplified product was cloned into the pCR II-vector of TA cloning kit (Invitrogen) and sequenced using standard techniques. The nucleotide sequence of the human VEGF-B cDNA clone is shown in FIG. 10 (SEQ ID NO:10), and the deduced amino acid sequence of human VEGF-B$_{167}$ is shown in FIG. 11 (SEQ ID NO:11).

The full length mouse cDNA clone of Example 2 and the full length human cDNA clone of Example 4 each encode a polypeptide of 188 amino acids containing an N-terminal hydrophobic putative signal sequence. In analogy with VEGF, the signal peptidase cleavage site is believed to be located between Ala 21 and Pro 22. The putative cleavage site of the signal peptidase is indicated in FIG. 16 by an arrow. Accordingly, the processed VEGF-B polypeptides of these two clones each contain 167 amino acids.

EXAMPLE 5

The clone which exhibited the 340 bp Spe1/BamH1 fragment isolated in Example 2 was analyzed, and the major portion was found to be identical to the first two clones of Example 2 which exhibited the 240 bp Spe1/BamH1 fragment. The difference is due to the presence of an insertion in the C-terminal part of the sequence.

This 340 bp Spe1/BamH1 DNA fragement encodes a further isoform of mouse VEGF-B containing 207 amino acids. The coding portion of the DNA encoding this protein (SEQ ID NO:12) is illustrated in FIG. 12, and the translated amino acid sequence (SEQ ID NO:13) is illustrated in FIG. 13. After cleavage of the 21 amino acid leader sequence, the mature protein contains 186 amino acids and is referred to as mVEGF-B$_{186}$. This isoform is clearly a result of alternative DNA splicing as described below with reference to FIG. 17.

EXAMPLE 6

The H.1 clone isolated as described in Example 4 was found to encode a 207 amino acid isoform of human VEGF-B. The coding portion of the DNA (SEQ ID NO:14) encoding this protein is illustrated in FIG. 14 and the translated amino acid sequence (SEQ ID NO:15) is illustrated in FIG. 15. Again, this isoform, which is designated hVEGF-B$_{186}$, appears to be a product of alternative splicing.

Both the mVEGF-B$_{186}$ of Example 5 and the hVEGF-B$_{186}$ of Example 6 include a 101 base pair insertion between nucleotides 414 and 415 of the coding sequence of VEGF-B$_{167}$. Following the insertion, the nucleotide sequences of these cDNA clones were identical to the correponding VEGF-B$_{167}$ sequences. The position of the 101 base pair insertion corresponds to the exon 5-exon 6 junction in VEGF. The insertion results in a frameshift which causes the C-terminal domains of the two VEGF-B isoforms to be entirely different.

The divergence of the C-terminal amino acid sequences starting at amino acid 116 in SEQ ID NOS 11 and 15, which correspond to the two principal VEGF-B isoforms, VEGF-B$_{167}$ and VEGF-B$_{186}$, is reflected by the different biochemical characteristics of the two isoforms. The C-terminal domain of VEGF-B$_{167}$ is strongly basic (net charge +13) and binds heparin. The C-terminal domain of VEGF-B$_{186}$ is weakly basic (net charge +5) and has a long stretch of hydrophobic amino acid residues in its C-terminus. The hydrophobic tail in VEGF-B$_{186}$ is unlikely to behave as a transmembrane domain since this variant of VEGF-B is secreted from cells. Therefore, despite an identical N-terminal domain, these two principal isoforms of VEGF-B have very different biochemical properties. The absence of the highly basic heparin-binding domain from VEGF-B$_{186}$ allows the protein to be freely secreted from cells. However, the secretion of VEGF-B$_{186}$ is remarkably slow; in a pulse chase experiment using transfected cells, VEGF-B$_{186}$ homodimers were not found in the medium before 1 hour. In contrast, VEGF homodimers and VEGF-B$_{186}$•VEGF dimers appear in the medium within 30 minutes.

FIG. 16 shows the aligned amino acid sequences of mouse and human VEGF-B$_{167}$ and VEGF-B$_{186}$ (SEQ ID NOS:5, 11, 13 & 15) in one-letter code. Identical residues are enclosed in boxes, while amino acid residues which differ between mouse and human VEGF-B$_{167}$ and VEGF-B$_{186}$ isoforms are outside the boxes. Mouse and human VEGF-B display approximately 88% amino acid sequence identity and are highly basic, especially in their C-terminal regions. The C-terminal domains of murine and human VEGF-B$_{186}$ are approximately 85% identical at the amino acid level. The C-terminal domains of murine and human VEGF-B$_{167}$ are approximately 84% identical at the amino acid level. Both polypeptides lack the consensus sequence for N-linked glycosylation (N-X-T/S). The arrow indicates the putative cleavage site for the signal peptidase between $Ala^{21}$ and $Pro^{22}$. Excluding the signal sequences, the mouse and human VEGF-$B_{167}$ amino acid sequences are highly homologous with only 20 replacements out the the 167 residues. The replacements are clustered in the N-terminus, in two regions around amino acids 60 and 145. All cysteine residues in both VEGF-$B_{167}$ proteins are invariant, but the eight cysteine residues in the C-terminal end of VEGF-$B_{167}$ are not conserved in the VEGF-$B_{186}$ isoforms. It is notable that the mouse and human sequences in the region between residues 66 and 129 are identical apart from one evolutionarily conserved replacement (Q105R). This is of importance since the receptor binding domains are found within this portion of the protein (compared to PDGF structure). From this it can be concluded that it is likely that mouse and human VEGF-B will exhibit cross-reactive binding on the receptor level and thus display identical or similar biological activities.

EXAMPLE 7

Exon-Intron Structures of Mouse and Human VEGF-B Genes

The structure of the human VEGF-B gene was determined by restriction mapping and nucleotide sequence analysis of cloned PCR fragments obtained from PCR reactions employing human genomic DNA as the template, except in the case of the first exon and intron, which were identified from a genomic λ-clone. The structure of the mouse gene was determined by restriction mapping and nucleotide sequence analysis of cloned PCR fragments amplified using different combinations of primers. As a template in these PCR amplifications an isolated genomic λ clone containing the entire mouse VEGF-B gene was used.

Procedure.

Several λ clones for the mouse VEGF-B gene were isolated from a 129/Sw λFIX genomic library as recommended by the supplier (Stratagene, Inc.). The ≈0.9 kb SalI/NotI insert of the pcif2 cDNA for VEGF-B (SEQ ID NO:1) was used as the probe. λ DNA from several positive clones were isolated from plate lysates. One of the positive λ-clones (clone 10) was subcloned as BamH1 fragments into pBluescript SK (Stratagene Inc.). Isolated DNA from this same clone was also used as the template in PCR reactions (100 ng of λ DNA/reaction) and the coding parts of the mouse VEGF-B gene were amplified using different combinations of primers. The nucleotide sequences of these primers were derived from the cDNA clones encoding murine VEGF-$B_{167}$ and murine VEGF-$B_{186}$. Taq DNA polymerase (2.5 U/reaction) was used. The generated PCR fragments were directly cloned into the TA-cloning vector pCR II (Invitrogen Inc.). The exon-intron structure of the mouse VEGF-B gene was established by nucleotide sequence analysis of the subcloned Bam H1 genomic fragments and of the cloned PCR products.

A human genomic λ-clone was isolated by screening $1 \times 10^6$ clones of a human genomic library in EMBL-3 SP6/T7 (Clontech) using high stringency conditions with a 90 bp PCR-fragment spanning 5' sequences of human VEGF-B cDNA as the probe. The washing conditions were: one wash at 1×SSC at room temperature for 30 minutes and two washes at 1×SSC at 65° C. for 30 minutes. Primers for the PCR were:

```
5'-CACCATGAGCCCTCTGCTCC-3'    (SEQ ID NO:18)
(forward) and

5'-GGGCATCAGGCTGGGAGACAG-3'.  (SEQ ID NO:19)
(reverse)
```

The positive λ-clone was subcloned as SacI fragments into pGEM 3Z vector (Promega) and was found to carry the 5'-region of the gene. The remaining parts of the human VEGF-B gene were amplified by PCR using genomic DNA as the template. Different combinations of primers derived from the human cDNA sequence were used. Dynazyme DNA polymerase (2.5 U/reaction, Finnzymes) was used. The amplified PCR fragments were directly cloned into the TA-cloning vector pCR II (Invitrogen Inc.). The exon-intron boundaries and the length of the short introns of the mouse and human VEGF-B genes were determined by nucleotide sequence analysis using vector specific primers or suitable primers derived from the cDNA sequences. The length of the larger introns were calculated based on the length of the amplified PCR fragments when analyzed by agarose gel electrophoresis.

Results.

The results showed that the coding parts of the mouse and human VEGF-B genes span approximately 4 kb of DNA and both genes are divided into seven coding exons ranging from 19 bp (E7) to 236 bp in length (E6). FIG. 17 is a schematic representation of the structures of the mouse and human genes for VEGF-B. The exon sizes in base pairs are noted inside the boxes, and the sizes of the introns are noted between the boxes. The introns are not shown to scale. The structures of the untranslated flanking regions of mouse and human VEGF-B genes were not established and are represented by gray boxes. The exon-intron junctions in both genes are listed in the following Table 3:

TABLE 3

(Donor sites are disclosed as SEQ ID NOS 32, 34, 36, 38, 40, 40, 43, 45, 47, 49, 51, 53, 40 & 56 respectively in order of appearance; Acceptor sites are disclosed as SEQ ID NOS 33, 35, 37, 39, 41, 42, 44, 46, 48, 50, 52, 54, 55 & 57 respectively in order of appearance)

| Exon | Length | Donor Site | Intron Length (bp) | Acceptor Site |
|---|---|---|---|---|
| | | Mouse | | |
| E1 | 60 | T CGC ACC CAG/gtacgtgcgt<br>a Arg Thr Gln | ≈590 | tttcccacag/GCC CCT GTG T<br>==========Ala Pro Val S |
| E2 | 43 | CAG AAG AAA G/gtaataatag<br>Gln Lys Lys V | 287 | ctgcccacag/TG GTG CCA TG<br>==========al Val Pro Tr |

TABLE 3-continued (Donor sites are disclosed as SEQ ID NOS 32, 34, 36, 38, 40, 40, 43, 45, 47, 49, 51, 53, 40 & 56 respectively in order of appearance; Acceptor sites are disclosed as SEQ ID NOS 33, 35, 37, 39, 41, 42, 44, 46, 48, 50, 52, 54, 55 & 57 respectively in order of appearance)

| Exon | Length | Donor Site | Intron Length (bp) | Acceptor Site |
|---|---|---|---|---|
| E3 | 197 | C CGA ATG CAG/gtaccagggc<br>l Arg Met Gln | 161 | ctgagcacag/ATC CTC ATG A<br>===========Ile Leu Met I |
| E4 | 74 | GT GAA TGC AG/gtgccagcca<br>ys Glu Cys Ar | 178 | ctcctcctag/G GTT GCC ATA<br>===========g Val Ala Ile | mVEGF-B$_{186}$

| Exon | Length | Donor Site | Intron Length (bp) | Acceptor Site |
|---|---|---|---|---|
| E5 | 36 | AG CCA GAC AG/gtgagttttt<br>ys Pro Asp Ar | ~200 | ctcctcctag/G GTT GCC ATA<br>===========g Val Ala Ile |
| E6A | 211 | Stop codon in exon 6<br>(TAG) | — | — | mVEGF-B$_{167}$

| Exon | Length | Donor Site | Intron Length (bp) | Acceptor Site |
|---|---|---|---|---|
| E5 | 36 | AG CCA GAC AG/gtgagttttt<br>ys Pro Asp Se | ~300 | cccactccag/C CCC AGG ATA<br>===========r Pro Arg Ile |
| E6B | 135 | AC ACC TGT AG/gtaaggagtc<br>sp Thr Cys Ar | ~2.6 kb | cactcccag/G TGC CGG AAG<br>===========g Cys Arg Lys |
| E7 | 19 | Stop codon in exon 7<br>(TGA) | — | — |

Human

| Exon | Length | Donor Site | Intron Length (bp) | Acceptor Site |
|---|---|---|---|---|
| E1 | 60 | C CCC GCC CAG/gtacgtgcgg<br>a Pro Ala Gln | ~760 | tctcccacag/GCC CCT GTC T<br>===========Ala Pro Val S |
| E2 | 43 | CAG AGG AAA G/gtaatactta<br>Gln Arg Lys V | 275 | ctgctcccag/TG GTG TCA TG<br>===========al Val Ser Tr |
| E3 | 197 | C CGG ATG CAG/gtactgggca<br>l Arg Met Gln | 244 | ctgagcacag/ATC CTC ATG A<br>===========Ile Leu Met I |
| E4 | 74 | GT GAA TGC AG/gtgccagcca<br>ys Glu Cys Ar | ~710 | tacttttcag/A CCT AAA AAA<br>===========g Pro Lys Lys | hVEGF-B$_{186}$

| Exon | Length | Donor Site | Intron Length (bp) | Acceptor Site |
|---|---|---|---|---|
| E5 | 35 | AG CCA GAC AG/gtgagtcttt<br>ys Pro glu Ar | 200 | tcctccctag/G GCT GCC ACT<br>===========g Ala Ala Thr |
| E6A | 211 | Stop codon in exon 6<br>(TAG) | — | — | hVEGF-B$_{167}$

| Exon | Length | Donor Site | Intron Length (bp) | Acceptor Site |
|---|---|---|---|---|
| E5 | 36 | AG CCA GAC AG/gtgagtcttt<br>ys Pro Glu Se | ~300 | cccactccag/C CCC AGG CCC<br>===========r Pro Arg Pro |
| E6B | 135 | AC ACC TGC AG/gtaggtttgg<br>sp Thr Cys Ar | 736 | ccctcctcag/G TGC CGG AAG<br>===========g Cys Arg Lys |
| E7 | 19 | Stop codon in exon 7<br>(TGA) | — | — |

As previously stated, exon 6 contains an alternative splice acceptor site which enables the gene to produce two different transcripts for VEGF-B isoforms. VEGF-B$_{167}$ uses exons 1-5, the last part of exon 6, and exon 7 (TGA). VEGF-B$_{186}$, uses exons 1 through 5, the first part of exon 6, and terminates in the last part of exon 6 (TAG). Exon 7 is not translated in VEGF-B$_{186}$ since the insertion of the first part of exon 6 introduces a frame shift and gives rise to a stop codon in the last part of exon 6. The position of the stop codon (TAG) for VEGF-B$_{186}$ is marked in exon 6B, and the stop codon (TGA) for VEGF-B$_{167}$ is marked in exon 7.

The introns in both genes vary from 161 bp to approximately 2.6 kb. The length of each exon and the locations of the splice junctions in the two genes were identical, and all splice donor and acceptor sites follow the canonical GT/AG rules, Padgett et al., *Annual Rev. of Biochemistry*, 55:1119-50 (1986). The only notable difference between the mouse and the human genes are the length of introns 1, 4 and 6 which are longer in the mouse gene. All exon-intron boundaries were found to be conserved between VEGF-B and VEGF, but the introns in the VEGF-B genes were generally smaller than in the VEGF gene.

The 300 bp-intron after the exon 5 in VEGF-B differs from the corresponding one in VEGF, which is 3 kb in length and contains an alternatively spliced exon found in the transcripts for $VEGF_{189}$ and $VEGF_{206}$, encoding many basic amino acid residues. When this intron in VEGF-B was analyzed more carefully, no exon corresponding to the 6th exon of VEGF could be found. Instead, the 3' end of this intron and the following exon were found to be identical with the corresponding sequences of the cDNA clones encoding $VEGF-B_{186}$. This is explainable by the fact that the mRNA for $VEGF-B_{186}$ is formed by use of an alternative splice acceptor site during mRNA splicing, resulting in an insertion of a 101 bp intron sequence into these mRNAs.

FIG. 18 shows a comparative hydrophilicity analysis of murine $VEGF-B_{167}$ and $VEGF-B_{186}$. The profiles were generated according to Kyle and Dolittle using a window of nine (9) residues. As would be expected, the pattern of hydrophilicity/hydrophobicity is essentially identical from amino acid 1 through amino acid 115. After amino acid 115, the hydrophilicity/hydrophobicity patterns diverge because of the frame shift introduced by the first part of exon 6. Thus, $VEGF-B_{167}$ and $VEGF-B_{186}$ can be expected to exhibit both similar and dissimilar activities.

Figure 19:
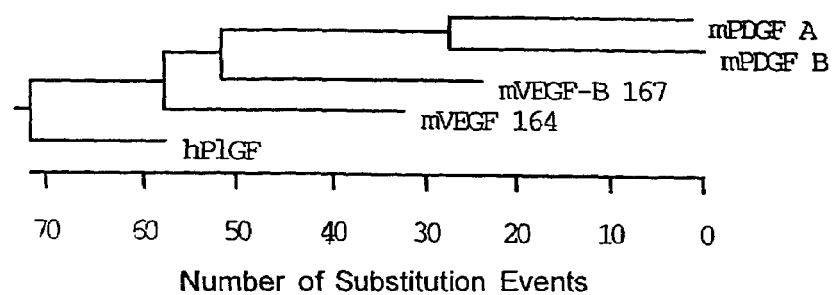
FIG. 19 shows a phylogenetic analysis of the VEGF/PDGF family of growth factors.

FIG. 19 is a dendrogram showing the phylogenetic relationship of the amino acid sequences of five members of the VEGF/PDGF family of growth factors. The number of replacements or substitutions decreases from the left to the right of the chart. It can be seen that VEGF-B lies between VEGF and the platelet derived growth factor (PDGF) group.

The multiple amino acid sequence alignments of FIGS. 9 and 16 and the phylogenetic analysis of FIG. 19 were carried out accoring to Hein, *Methods in Enzymology*, Vol. 183, pp. 626-45, Academic Press Inc., San Diego (1990) using the PAM 250 distance table.

EXAMPLE 8

Antibody Production a. Antiserum to Mouse VEGF-B.

Antisera to mouse VEGF-B were raised by immunizing rabbits with a 18-mer oligopeptide comprising the N-terminal region of processed VEGF-B, coupled to keyhole limpet hemocyanin. Cysteine residues were introduced as the N-terminal and C-terminal amino acid residues to allow coupling of the peptide to the carrier protein using SPDP (Pharmacia). The sequence of the oligopeptide was

C-P-V-S-Q-F-D-G-P-S-H-Q-K-K-V-V-P-C. (SEQ ID NO:21)

Each rabbit received a subcutaneous injection with 300 µg of the peptide conjugate emulsified in Complete Freunds Adjuvant. Subcutaneous booster injections were given every second week with the same amount of antigen emulsified in Incomplete Freunds Adjuvant. Sera were obtained after the second booster injections.

b. Antiserum to Human VEGF-B.

Antipeptide antiserum to human VEGF-B was generated by immunizing rabbits with a branched 23-mer oligopeptide comprising the following N-terminal region amino acid residue sequence (SEQ ID NO:22):

S-Q-P-D-A-P-G-H-Q-R-K-V-V-S-W-I-D-V-Y-T-R-A-T.

The branched 23-mer oligo peptide was synthesized according to Tam, "Synthetic peptide vaccine design: synthesis and properties of a high-density multiple antigenic peptide system", *Proc. Natl. Acad. Sci. USA*, Vol. 85, pages 5409-413 (1988). In the first immunization, rabbits were subcutaneously injected with 500 µg of the branched peptide emulsified in Complete Freunds Adjuvant. In the subsequent boosters, 200 µg of the antigen emulsified in Incomplete Freunds Adjuvant was injected. Antisera were collected after the second and third boosters by conventional techniques.

EXAMPLE 9

Biochemical Properties of $VEGF-B_{167}$, Homo-Dimerization, and Heterodimerization with VEGF The biochemical properties of human $VEGF-B_{167}$ were examined in transfected human embryonic kidney 293EBNA cells (Invitrogen, Inc.). cDNA inserts encoding human $VEGF-B_{167}$ and human $VEGF_{165}$ [see Keck et al., *Science*, Vol. 246, pages 1309-312 (1989)] were individually cloned into the pREP7 expression vector (Invitrogen, Inc.). Human embryo kidney 293EBNA cells (expressing Epstein-Barr virus nuclear antigen-1) were transfected by transient transfection with the respective expression plasmids using calcium phosphate precipitation, and the cells were incubated for 48 hours. As a control, cells also were transfected with an expression vector containing the $VEGF-B_{167}$ cDNA in reverse orientation. Monolayers of cells were incubated in methionine-free and cysteine-free medium for 30 minutes followed by labeling with 100 µCi/ml [$^{35}$S]methionine and [$^{35}$S]cysteine (Promix, Amersham Inc.) in the same medium for 2 hours. The labeling medium was replaced with normal medium without serum, and labelled proteins were chased for 6 hours. Heparin was included during the chase when indicated (100 µg/ml). Media were collected after the chase period, and cells were solubilized in 10 mM Tris pH 7.5, 50 mM NaCl, 0.5% sodium deoxycholate, 0.5% Nonidet P-40, 0.1% SDS and 0.1 U/ml aprotinin.

$VEGF-B_{167}$ was expressed in the cells transfected with the plasmids containing the $VEGF-B_{167}$ DNA. Aliquots of the culture supernatants from cells treated or untreated with heparin and detergent solubilized cell lysates were subjected to immunoprecipitation with the specific antipeptide antiserum to VEGF-B obtained as described in Example 8 and analyzed by SDS-PAGE under reducing conditions unless otherwise indicated. The data show that $VEGF-B_{167}$ homodimers and $VEGF-B_{167}$-$VEGF_{165}$ heterodimers are released from cells by heparin. By heparin treatment (1-100 µg/ml) or 1.2 M NaCl, $VEGF-B_{167}$ was released from cells and found in the supernatant. If cells were not treated with heparin, $VEGF-B_{167}$ remained cell-associated and was not released into the culture medium. Under the same conditions, $VEGF_{165}$ homodimers are secreted from the cells and found in the culture supernatants without heparin treatment.

Under reducing conditions, human $VEGF-B_{167}$ migrated with a Mr of 21 kDa. Analysis of culture supernatants under non-reducing conditions showed that $VEGF-B_{167}$ migrated as an Mr 42 kDa species indicating a dimeric structure. These results suggest that $VEGF-B_{167}$ forms disulfide-linked dimers associated with the cell surface, probably through ionic interactions with extracellular heparan sulfate proteoglycans. The association is likely to be mediated by the C-terminal basic domain, as observed for the longer splice variants of VEGF.

Since VEGF has been shown to form heterodimers with PlGF, it was decided to test whether $VEGF_{165}$ could also form heterodimers with $VEGF-B_{167}$. For this purpose 293EBNA cells were co-transfected with expression vectors encoding both human $VEGF_{165}$ and human $VEGF-B_{167}$, and $VEGF-B_{167}$ was expressed in combination with $VEGF_{165}$. Metabolically labelled proteins were chased in the presence of heparin, and immunoprecipitations were carried out with antisera to either $VEGF-B_{167}$ or $VEGF_{165}$. The antiserum to human VEGF was from R&D Systems. Under non-reducing conditions the $VEGF-B_{167} \cdot VEGF_{165}$ heterodimers migrated as Mr 42-46 kDa species. The results show that VEGF-B can form disulfide linked heterodimers with VEGF, which, in the absence of heparin, remain cell-associated. Since homodimers of $VEGF_{165}$ are efficiently secreted into the media, VEGF-B appears to determine the secretion of the heterodimer.

VEGF-B is synthesized normally in the endoplasmic reticulum of the source cell for subsequent export. Recombinant VEGF-B may be produced by inserting a DNA sequence encoding the VEGF-B protein together with suitable operatively linked promoter and control sequences into a suitable vector, such as the well known plasmid pBR322 or a derivative thereof, transforming or transfecting a suitable host cell, such as *E. coli* or a Cos cell, with the resulting vector or other systems well known in the art, screening the resulting transformants or transfectants for VEGF-B expression, and then culturing cell lines or bacterial cell strains which are positive for the expression of VEGF-B. Either a eukaryotic vector or a prokaryotic vector may be used, depending on the type of cell which is to be transfected or transformed therewith. A particularly preferred system for production of recombinant VEGF-B is the baculovirus-insect cell system, which has proved capable of producing excellent yields of recombinant protein.

EXAMPLE 10

VEGF-B Expression Using the Baculovirus System 10.1 VEGF-B with its Own Signal Peptide.

a) Cloning and Transfection.

The complete human $VEGF-B_{167}$ gene was inserted into a commercially available plasmid pCRII (Invitrogen Corp.). The HindIII-XbaI fragment from the resulting plasmid $pCRII-VEGF-B_{167}$, which encodes the whole open reading frame of $VEGF-B_{167}$ then was cloned into pFASTBAC1, and both the 3'- and 5'-junctions were sequenced. Bacmid-DNA was prepared according to the manufacturers instructions for the "Bac-To-Bac™ Baculovirus Expression System" (Life Technologies Inc.) and lipofected to Sf900II-adapted Sf9 cells (obtained from Dr. Christian Oker-Blom). Sf9 cells are from the American Type Culture Collection Cell Repository Line Bank, Rockville Md. (ATCC CRL-1711). The transfected cells were then cultured on standard TMN-FH medium in 25 $cm^2$ culture dishes.

b) Assay for Protein Expression.

About 72 hours after transfection, the cells were lysed and 1 ml of culture supernatant and the cell lysate were assayed for expressed VEGF-B by immunoprecipitation as described in Example 9 and Western blotting. Lysates from three out of four independently transfected cell cultures were found positive for VEGF-B, although the intensity of the signal in the Western blot varied. The expressed VEGF-B polypeptide in each case was found to correspond in size to the protein expressed in mammalian cells in Example 9.

The viral stock from the cells that gave the strongest signal in Western blotting was amplified two rounds by infecting cells and collecting new virus from the medium. The resulting supernatant was analyzed. Uninfected cells were also analyzed as a negative control. Time course analysis showed that cells harvested between 48 and 72 hours after infection contained the greatest amount of VEGF-B. After 96 hours post infection, as a result of virus-induced cell lysis, VEGF-B could also be detected in the culture supernatant by immunoprecipitation and Western blotting. Recombinant VEGF-B could be precipitated from the lysate between 20% and 40% $(NH_4)_2SO_4$.

10.2 VEGF-B with the Melittin Signal Peptide (pVTBac).

a) Cloning and Transfection.

A polymerase chain reaction (PCR) fragment from nucleotide position 68 to 141 was used to introduce a BamHI restriction site immediately after the signal cleavage site in the plasmid $pCRII-VEGF-B_{167}$ from Example 10.1. The BamHI fragment from this modified $pCRII-VEGF-B_{167}$ construct was cloned into BamHI opened pVTBac [Tessier et al., "Enhanced secretion from insect cells of a foreign protein fused to the honeybee mellitin signal peptide", *Gene*, Vol. 98, page 177 (1991)]. Both 3'- and 5'-junctions were sequenced. Sf9 cells were cotransfected with the aforedescribed pVTBac vector which contained the human $VGEF-B_{167}$ gene, and with linearized baculovirus DNA (Insectin™, Invitrogen Corp.). The transfected cells then were cultured in TMN-FH medium.

b) Assay for Protein Expression.

Forty-eight hours after transfection, the supernatant was collected and subjected to primary screening by immunoprecipitation. Four positive plaques were isolated.

10.3 A cDNA insert encoding murine $VEGF-B_{186}$ (EcoR1 cut cDNA fragment from a murine $VEGF-B_{186}$ cDNA (SEQ ID NO:12) clone) was cloned into pFASTBAC 1. An EcoR1 cut cDNA fragment from murine $VEGF-B_{167}$ (SEQ ID NO:4) was also cloned into pFASTBAC 1. The resulting plasmids were transformed into bacteria as described in 10.1 above, and recombined plasmids were isolated and lipofected into Sf9 and Sf21 cells. Supernatants containing recombinant baculovirus were amplified by several rounds of reinfection of Sf21 cells. The final titers of the baculovirus stocks were determined by plaque titration and found to vary between $4 \times 10^8$ and $2 \times 10^9$ baculovirus particles per milliliter of stock supernatant.

EXAMPLE 11

Large Scale Production of Recombinant VEGF-B

Sf21 cells [see Vaughn et al., *In Vitro*, 13:213-17 (1977)] were infected with the baculovirus stocks of Example 10 at a multiplicity of infection of 10 virus particles per cell. The infected Sf21 cells were grown in roller flasks and seeded at a density of $2 \times 10^6$ cells per ml of serum free medium (Sf900II, Gibco-BRL) for 96 hours. Culture media and cells were then harvested. Aliquots of the cell lysates and of the media were analyzed by SDS-PAGE. Total protein patterns were visualized by staining the gels with Coomassie Brilliant Blue and the presence of expressed VEGF-B isoforms were visualized by immunoblotting using specific antipeptide antibodies to human and mouse VEGF-B as described above in Example 8. The analysis revealed that both human and mouse VEGF-$B_{167}$ polypeptides were of the expected sizes of 21.5 kDa. Both proteins were retained intracellularly in the infected cells and not released into the medium. In contrast, mouse VEGF-$B_{186}$ was readily secreted into the medium in a dimeric form. The VEGF-$B_{186}$, homodimers migrated as a 52-54 kDa species which suggested that insect cell produced protein did not undergo the same covalent modification as found for VEGF-$B_{186}$ secreted from transfected Cos-1 cells.

EXAMPLE 12

Transfection and Analysis of Cos-1 Cells Expressing VEGF-$B_{186}$ cDNA inserts encoding mouse VEGF-$B_{186}$ and human VEGF$_{165}$ were cloned into the pSG5 expression vector [Green et al., *Nucleic Acid Res.*, 16:369 (1988)]. Cos-1 cells were maintained in minimal essential medium (MEM) containing 10% fetal calf serum, 2 mM glutamine and appropriate antibiotics. For transfections, the cells were replated into 90 mm Petri dishes. The cells were transfected with the expression vectors, separately or in combination, using calcium phosphate precipitation and incubated for 36-48 hours. Monolayers of cells were incubated in medium free of methionine and cysteine for 30 min and then incubated in the same medium containing 100 μCi/ml of [$^{35}$S]-methionine and [$^{35}$S]-cysteine for 2 hours (Promix Amersham Inc.).

For the pulse-chase experiments, the cells were labeled for 30 minutes, washed twice with normal medium and then incubated for up to 6 hours in MEM without fetal calf serum. Media were collected after the chase period and the cells were solubilized in 10 mM Tris buffer pH 7.5 containing 50 mM NaCl, 0.5% deoxycholate, 0.5% nonidet P-40 and 0.1% SDS. Aliquots of the media and the cell lysates were subjected to immunoprecipitation using the specific antiserum to mouse VEGF-B from Example 8a and a specific antiserum to human VEGF commercially available from R&D Systems. The precipitates were analyzed by SDS-PAGE.

EXAMPLE 13

Biochemical Properties of VEGF-$B_{186}$ Expressed in Transfected Cos-1 Cells

Figure 22:
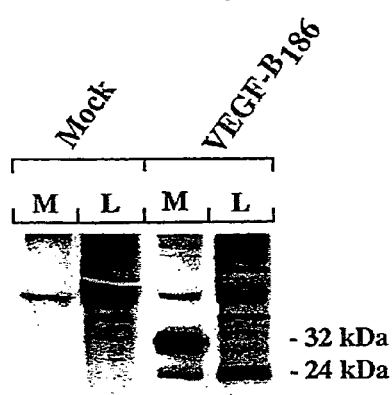
FIG. 22 shows the results of immunoprecipitation and SDS-PAGE analysis of cell culture media and detergent solubilized cell lysates from Cos-1 cells transiently transfected with a murine VEGF-B cDNA.

The biochemical properties of mouse VEGF-$B_{186}$ were examined in Cos-1 cells transiently transfected as described in Example 12 with an appropriate expression vector. The cells were metabolically labelled, and proteins from the labelled cells were immunoprecipitated using an antipeptide antibody to VEGF-B. The precipitated material was subjected to SDS-PAGE analysis under reducing conditions. Both the cell culture medium (M) and a detergent solubilized cell lysate (L) were analyzed. The results are shown in FIG. 22. It can be seen that cell associated VEGF-$B_{186}$ migrated as an approximately $M_r$ 24,000 polypeptide under reducing conditions. In contrast, VEGF-$B_{186}$ present in the medium of transfected cells migrated as a $M_r$ 32,000 species, suggesting that the protein was covalently modified during its intracellular transport and secretion. The corresponding molecules were not detected in cell lysates or media from mock transfected Cos-1 cells used as a control.

Immunoprecipitation of media and SDS-PAGE analysis under non-reducing conditions, showed an approximately $M_r$ 60,000 species suggesting that VEGF-$B_{186}$ formed disulfide-linked homodimers. Including 100 ug/ml of heparin during the labelling did not affect the secretion or release of VEGF-$B_{186}$ homodimers from the transfected cells.

EXAMPLE 14

Biosynthesis of VEGF-$B_{186}$ Homodimers

The biosynthesis of VEGF-$B_{186}$ homodimers was examined by pulse-chase experiments. Transfected Cos-1 cells were metabolically labelled for 30 minutes and then chased for up to 4 hours. Immunoprecipitation and SDS-PAGE analysis of detergent solubilized cell lysates and media showed that the cell-associated approximately $M_r$ 24,000 species was readily detected in the lysates throughout the chase period. The decrease in the intensity of this molecular species was associated with an increase in the $M_r$ 32,000 protein present in the media. The $M_r$ 32,000 species appeared in the medium after 1 hour of chase. Highest levels of secreted VEGF-$B_{186}$ were obtained after the 4 hour chase period No intermediates were detected in the cell lysates, but the secreted $M_r$ 32,000 protein appeared slightly heterogenous. The nature of the modification is presently unknown, but N-linked glycosylation can be excluded in the absence of consensus sites for this modification.

EXAMPLE 15

Formation of Heterodimers by VEGF-$B_{186}$

Figure 23:
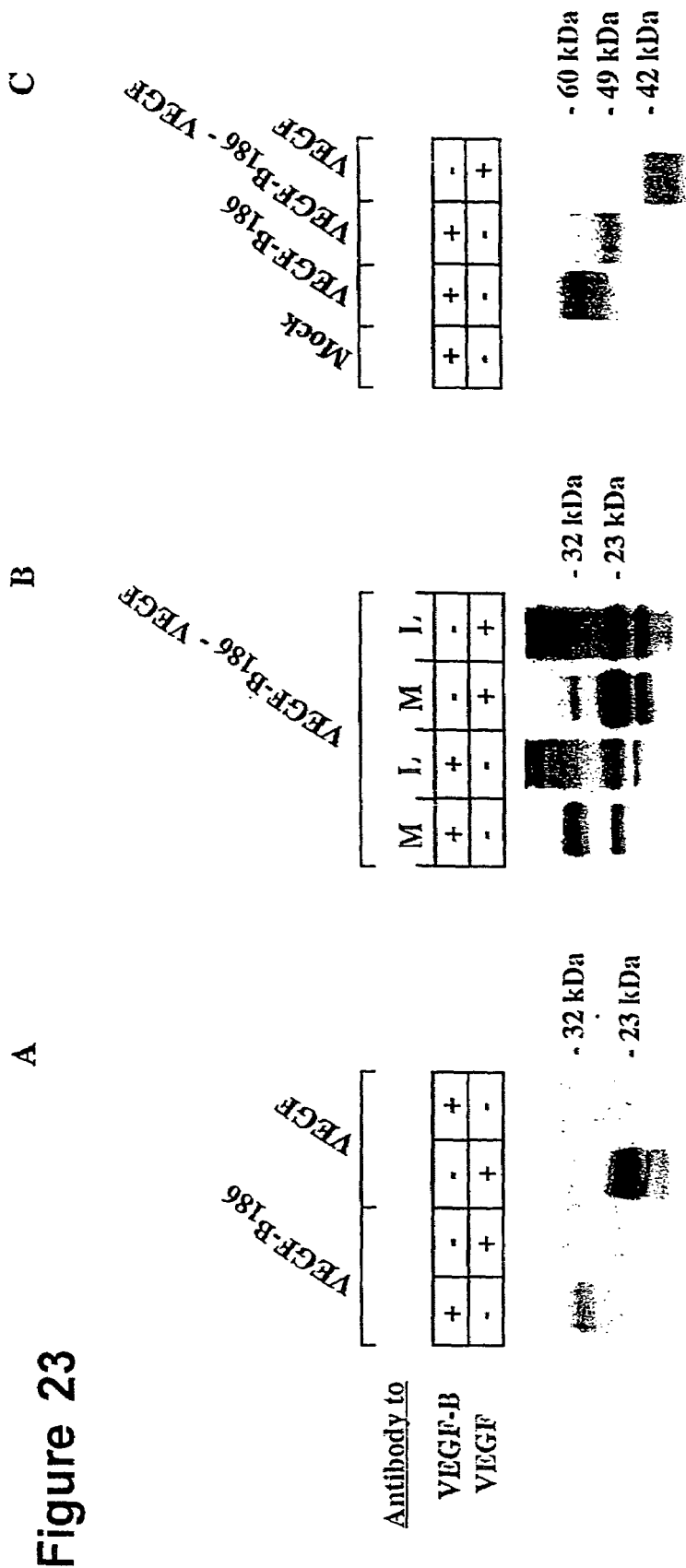
FIG. 23A shows the results of immunoprecipitation and SDS-PAGE analysis of cell culture media from transfected Cos-1 cells separately expressing murine VEGF-$B_{186}$ and human VEGF$_{165}$.
FIG. 23B shows the results of immunoprecipitation and SDS-PAGE analysis of cell culture media (M) and detergent solubilized cell lysates (L) of Cos-1 cells which coexpress murine VEGF-$B_{186}$ and human VEGF$_{165}$.
FIG. 23C shows the results of immunoprecipitation and SDS-PAGE analysis of cell culture media from Cos-1 cells expressing murine VEGF-$B_{186}$ and human VEGF, either separately or in combination, and from mock transfected control cells.

As noted above, VEGF-B and VEGF are coexpressed in many tissues and VEGF-$B_{167}$. VEGF$_{165}$ heterodimers are readily formed when coexpressed in transfected cells. To examine whether VEGF-$B_{186}$ also could form heterodimers with VEGF$_{165}$, Cos-1 cells were transfected as described above with the appropriate expression vectors, either alone or in combination. Metabolically labelled proteins present in the media from the transfected cells were subjected to immunoprecipitations using antisera to VEGF-B and VEGF. FIG. 23A shows the results of SDS-PAGE analysis under reducing conditions of the immunoprecipitates from the cell culture media of transiently transfected Cos-1 cells separately expressing VEGF-$B_{186}$ and VEGF, respectively. It can be seen that the antisera were specific for VEGF-B and VEGF, respectively, with no detectable cross-reactivity.

Cos-1 cells were cotransfected with expression vectors for VEGF-$B_{186}$ and VEGF$_{165}$. Cell culture media (M) and detergent solubilized lysates (L) from the resulting cells which coexpressed VEGF-$B_{186}$ and VEGF$_{165}$ were subjected to immunoprecipitation and SDS-PAGE analysis under reducing conditions. The results are shown in FIG. 23B. The test showed that murine VEGF-$B_{186}$ and human VEGF$_{165}$ form intracellular and secreted heterodimers.

Culture media from cells expressing murine VEGF-$B_{186}$ and human VEGF$_{165}$, either separately or in combination, were subjected to immunoprecipitation using antibodies to VEGF-B and VEGF and analyzed by SDS-PAGE under non-reducing conditions. As a control, cell culture medium from mock transfected cells was analyzed. The results are shown in FIG. 23C. It was found that VEGF-$B_{186}$ forms secreted disulfide-linked homodimers and that VEGF-$B_{186}$ and VEGF$_{165}$ together form secreted disulfide-linked heterodimers.

To analyze whether heterodimer formation with VEGF affected the secretion and release of VEGF-$B_{186}$, pulse-chase experiments were carried out using Cos-1 cells transiently transfected with expression vectors for VEGF-$B_{186}$ and VEGF$_{165}$. Cell associated disulfide-linked heterodimers could be recovered following the 30 minute labelling period, and secreted heterodimers were recovered from the medium already after a 30 minute chase period. The secreted heterodimers accumulated in the medium for up to 2 hours post labelling In the 4 hour chase time point there was a decrease in the amount of heterodimers in the medium, possibly due to the degradation of the complex. Some VEGF-$B_{186}$•VEGF heterodimers remained cell-associated throughout the chase. These results suggested that heterodimer formation with VEGF promoted the secretion of VEGF-$B_{186}$ compared to the secretion of VEGF-$B_{186}$ homodimers. Furthermore, the presence of heterodimers already following the 30 minute labelling period suggested that the slow release of VEGF-$B_{186}$ homodimers was not due an impaired ability of VEGF-$B_{186}$ to dimerize.

EXAMPLE 16

Purification of Secreted VEGF-$B_{186}$ Homodimers

Secreted VEGF-$B_{186}$ homodimers were isolated from serum free culture media of baculovirus infected Sf21 cells as follows:
 a. Initial Separation.
The major contaminating protein in the culture media was the baculovirus protein gp64/67, an acidic protein secreted by baculovirus infected cells. To remove this protein, the culture media was concentrated twenty-fold by ultrafiltration and then passed over a Sephadex G-25 column equilibrated in 20 mM phosphate buffer pH 6.5 containing 20 mM NaCL. Eluted proteins were then passed over a CM-Sepharose (Pharmacia) ion-exchange column equilibrated in the same buffer. The column was washed with the phosphate buffer to remove unbound proteins, and bound proteins were eluted by stepwise increasing the NaCl concentration of the elution buffer. The major gp64/67 baculovirus encoded protein did not bind to the ion-exchange column under those conditions while VEGF-$B_{186}$ homodimers eluted at a NaCl concentration of 90 mM. As judged by SDS-PAGE analysis of the eluted fraction, VEGF-$B_{186}$ homodimers were 5-15% pure by this procedure.
 b. Purification to Homogeniety.
The VEGF-$B_{186}$ homodimers are purified to homogeneity on a MonoS column coupled to a FLPC system (Pharmacia). Bound protein is eluted with a linear gradient of NaCl in 20 mM phosphate buffer pH 6.5.

EXAMPLE 17

In order to find out whether the two VEGF-B splice isoforms exhibited a differential tissue distribution and whether additional isoforms existed, an RT-PCR analysis was carried out using total RNA extracted from mouse brain, heart, liver and kidney and from human embryonic heart and skeletal muscle. The transcripts were analyzed by PCR using four pairs of specific primers covering exons 4 to 7 and exons 3 to 7 in the mouse and human VEGF-B genes, respectively.
 Procedure.
Total RNA from mouse and human tissues were isolated using standard procedures as disclosed by Chirgwin et al., *Biochemistry*, 18:5294-99 (1979). Two to five μg of total RNA per reaction were used for first strand cDNA synthesis using avian myelostosis virus reverse transcriptase (20 U/reaction). The reactions were primed with oligo-$(dT)_{18}$. Aliquots of these reactions were used as templates in PCR reactions using Taq DNA polymerase (2.5 U/reaction). To amplify mouse cDNA, two pairs of primers were used. These pairs were obtained by combining a common 5'-primer 5'-CACAGCCAATGTGAATGCA,        (SEQ ID NO:23)
    (forward)

located in exon 4 with two different 3'-primers

5'-GCTCTAAGCCCCGCCCTTGGCAATGGAGGAA (SEQ ID NO:24)
    (reverse) and

5'-ACGTAGATCTTCACTTTCGCGGCTTCCG   (SEQ ID NO:25)
    (reverse)

(this last primer has a Bgl II site and 4 extra bases in the 5' end) located in exons 6B and 7, respectively. Following analysis by agarose gel electrophoresis, the amplified bands were transferred onto a nylon filter (Genescreen Plus) and sequentially hydbridized with oligonucleotide probes specific for exons 6A and 6B. The oligonucleotide probes were 5'-CTCTGTTCCGGGCTGGGACTCTA (exon 6A) (SEQ ID NO:26) and 5'-TCAGGGCGTTGACGGCGCTGGGTG-CAA (exon 6B) (SEQ ID NO:27). The oligonucleotide probes were labeled with [$^{32}$P]dCTP using terminal transferase to high specific activity.

Hybridizations, using $1 \times 10^6$ cpm of labeled probe/ml of solution, were carried out at 37° C. in 6×SSC containing 5× Denhardt's solution, 0.5% SDS and 100 μg/ml of salmon sperm DNA. The filters were washed at the same temperature in 6×SSC containing 0.5% SDS for 2×15 min and exposed to film.

The two pairs of primers used for amplification of human cDNA were combined using two different 5'-primers, 5'-CCTGACGATGGCCTGGAGTGT,      (SEQ ID NO:28)
    (forward)

located in exon 3 and

5'-TGTCCCTGGAAGAACACAGCC,      (SEQ ID NO:29)
    (forward)

located in exon 4, with a common 3'-primer,

5'-GCCATGTGTCACCTTCGCAG        (SEQ ID NO:19)
    (reverse)

located in exon 7. Aliquots of the amplified products were analyzed by agarose gel electrophoresis. The aliquots were directly cloned in the TA-cloning vector pCR II (Invitrogen, Inc.), and generated plasmids were analyzed by nucleotide sequencing. Amplification of GAPDH served as a control.
 Results.
Analysis of amplified PCR products by agarose gel electrophoresis showed two major bands of 215 and 316 bp, respectively. These sizes are consistent with the two mRNAs corresponding to VEGF-$B_{167}$ and VEGF-$B_{186}$. These two bands were of the same intensity suggesting that the two isoforms were expressed at approximately equal levels in all mouse and human tissues examined.

To verify the identity of the amplified products from mouse tissues, the PCR-amplified DNA was transferred to a filter and probed with specific oligonucleotide probes for exons 6A and 6B, respectively. The autoradiograms showed that an exon 6-specific probe hybridized with the 316 bp band while the exon 6B specific probe hybridized with both the 215 bp and the 316 bp amplified bands. These results are consistent with the alternative usage of acceptor site in exon 6 to create the two isoforms of VEGF-B and thus all the amplified products corresponded to those predicted from the sequences of VEGF-B$_{167}$ and VEGF-B$_{186}$ isoforms.

Agarose gel electrophoresis of products of PCR analysis of total RNA isolated from human embryonic heart and muscle visualized two major amplified bands of 329 bp and 430 bp.

Taken together, these data demonstrate that VEGF-B$_{186}$, and VEGF-B$_{186}$ are the two major isoforms of VEGF-B in tissues The pattern of the PCR products and the location of the primers indicate that if any still longer splice isoforms exist for VEGF-B, such transcripts use a splice acceptor site located a little more 5' than in the case of VEGF-B$_{186}$. Furthermore, PCR products corresponding to VEGF$_{121}$, which lacks heparin binding domains, i.e. sequences corresponding to exon 6 in VEGF-B, were not detected. However, splicing of exon 5 to exon 7 would give rise to a transcript encoding an isoform of VEGF-B corresponding to VEGF$_{121}$, and this putative isoform of VEGF-B might be expressed in tissues other than those analyzed in this example.

EXAMPLE 18

Stimulation of Cell Proliferation

The ability of VEGF-B$_{167}$ to stimulate endothelial cell proliferation was established through analysis of [$^3$H]thymidine incorporation in human umbilical vein endothelial cells (HUVEC) and in bovine capillary endothelial (BCE) cells.

293EBNA cells were transfected as described above with expression vectors for VEGF-B$_{167}$, VEGF$_{165}$ or empty vector (mock) in the presence of 1 µg/ml heparin. Conditioned media from these cells were diluted in respective media, applied to human umbilical vein endothelial cells (HUVEC) and to bovine capillary endothelial (BCE) cells and incorporation of [$^3$H]thymidine was measured. As a positive control recombinant bFGF was added to BCE cells.

To elaborate, conditioned media containing human VEGF-B and human VEGF$_{165}$ were collected from 293EBNA cells transfected with the appropriate expression vectors or with empty vector (mock) in the presence of heparin (1 µg/ml) 48 hours posttransfection. Second passage HUVEC were plated into 96-well plates (4×10$^3$ cells/well) in M-199 medium supplemented with 10% fetal bovine serum and incubated for 24 hours. Conditioned media were diluted with the growth medium, and cells were stimulated for 48 hours. Fresh conditioned media containing 10 µCi/ml of [$^3$H]thymidine (Amersham Inc.) were added to the cells, and stimulations were continued for another 48 hours. Cells were washed with PBS and trypsinized, and incorporated radioactivity was determined by liquid scintillation counting. BCE cells were seeded into 24-well plates and grown until confluence in minimal essential medium (MEM) supplemented with 10% fetal calf serum. Cells were starved in MEM supplemented with 3% fetal calf serum for 72 hours, after which conditioned media diluted into serum-free medium were added to the cells and the cells were stimulated for 24 hours. [$^3$H]Thymidine was included during the last 4 hours of the stimulation (1 µCi/ml). Stimulations with bFGF were carried out as above using 6 ng/ml of recombinant bFGF (Synergen Inc.). Cells were washed with PBS, lysed with NaOH, and incorporated radioactivity was determined by liquid scintillation counting.

Figure 20:
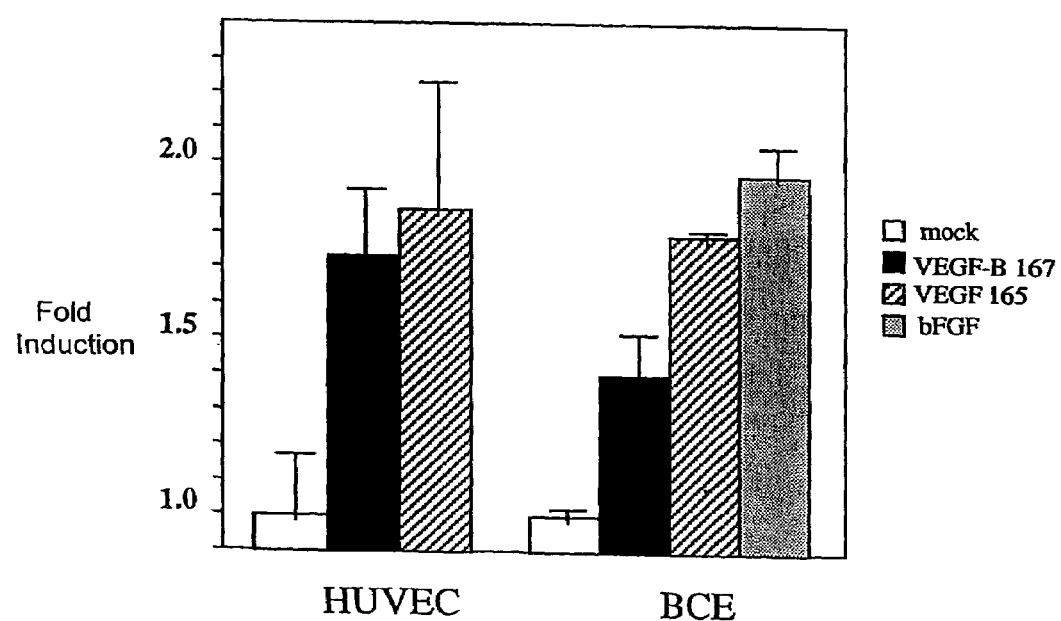
FIG. 20 is a graph showing the induction of [$^3$H]thymidine incorporation by VEGF-B, VEGF and bFGF for human umbilical vein endothelial cells (HUVEC) and bovine capillary endothelial (BCE) cells.

FIG. 20 is a bar graph showing fold of induction of [$^3$H]thymidine incorporation by VEGF-B$_{167}$ in human umbilical vein endothelial cells (HUVEC) and in bovine capillary endothelial (BCE) cells, as compared to basal activity induced by conditioned medium from the mock transfected cells. For comparison purposes, the induction by VEGF$_{165}$ and by bFGF are also shown. The bars show the mean±standard deviation of parallel samples. Similar results were obtained in several other independent experiments. The test results clearly show that VEGF-B induced [$^3$H] thymidine incorporation in both HUVEC and BCE cells and stimulated proliferation of endothelial cells in vitro, thereby demonstrating that VEGF-B is an endothelial growth factor.

EXAMPLE 19

Identification of Human VEGF-B Promoter DNA Clones and Activity

A human genomic DNA library in bacteriophage λ EMBL was screened using a 5' PCR fragment containing the sequences from the VEGF-B first and second exons as a probe. Two positive clones were obtained, and one of these was subcloned in the Bluescript SKII plasmid as Sac I fragments. A 1.4 kb fragment was obtained, which contained about 0.4 kb of sequences upstream from an Nco I site present in the cDNA (located less than 100 bp upstream of the ATG translational initiation site).

Figure 24:
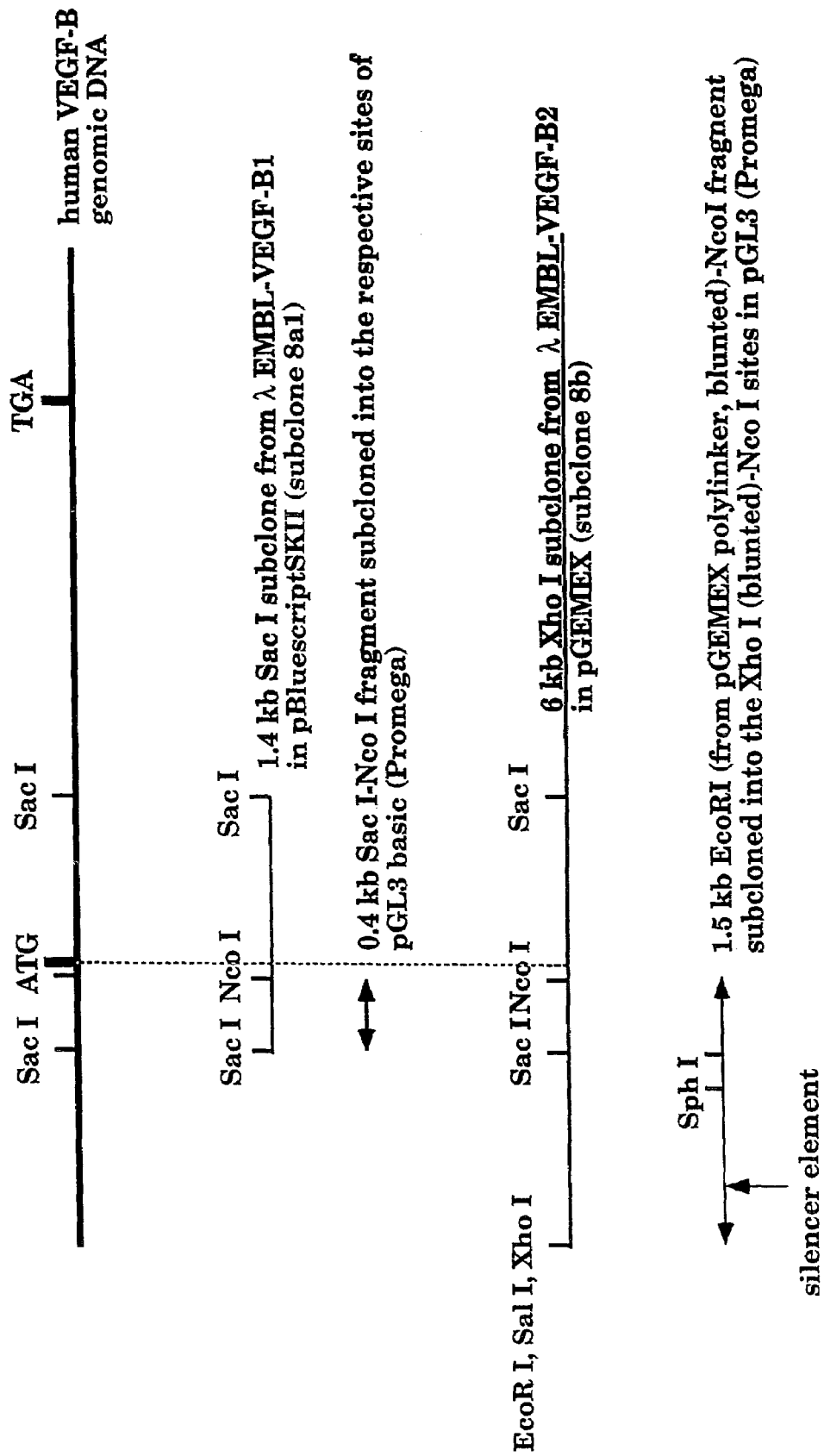
FIG. 24 is a schematic illustration of the derivation of VEGF-B promoter-reporter clones.

In addition, an XhoI fragment of about 6 kb from the other λ clone was subcloned into the pGEMEX plasmid. This subclone contained about 1.5 kb of sequences upstream from the NcoI site. The SacI/NcoI fragment and an EcoRI (polylinker)—NcoI fragment were subcloned into pGL3 basic vector (Promega) in the respective transcriptional orientation. DNA of these subclones, and from the pGL3 control vector containing the SV40 promoter, was transfected into HeLa cells using calcium phosphate precipitation. Two days after transfection, the luciferase activities were measured from lysates of the transfected cells. The results indicated that the 400 bp SacI/NcoI fragment has promoter activity equal to about 30% of the activity of the pGL3 control vector, while the 1.5 kb fragment gave only background activity. Use of a stronger or more active promoter, for example the CMV promoter or the elongation factor 1-alpha promoter, would probably give higher activity in human cells and tissues. The structure of the cloned fragments is illustrated in FIG. 24.

The 1.5 kb fragment upstream of the Nco I site was sequenced. The resulting sequence (SEQ ID NO:17) is illustrated in FIG. 25. The sequence obtained revealed a putative silencer element [Weissman and Singer, *Molecular and Cellular Biology*, 11:4228-234 (1991)] composed of two eight-base pair stretches between nucleotides 166-187 (boxed in the drawing). This silencer may be responsible for the relative lack of activity of the 1.5 kb fragment.

EXAMPLE 20

Analysis of VEGF-B mRNA in Melanomas, Normal Skin and Muscle by RT-PCR

Normal skin and melanoma tissues were obtained from patients attending the Department of Radiotherapy and Oncology, Helsinki University Central Hospital. Four metastatic melanoma specimens were obtained freshly after surgical excision, immediately embedded in Tissue-tek (Miles) and frozen in liquid nitrogen. Samples of normal skin were obtained from volunteer patients undergoing surgery for mammary carcinoma and excision of a cutaneous naevus. All specimens were inspected by a pathologist to confirm the diagnosis.

Total RNA was isolated by the guanidium isothiocyante procedure [Chomczynski et al., *Anal. Biochem.* 162:156-159 (1987)]. cDNA was synthesized using 0.2 µg of random hexadeoxynucleotide primers, 5 units of murine reverse transcriptase, 5 µg of total RNA as a template and a first-strand cDNA synthesis kit (Pharmacia). After incubation at 37° C. for 1 hour, the reaction mixture was stored at −70° C. Negative control samples for PCR amplification were prepared similarly except that reverse transcriptase was not added. β-actin also was tested as an internal standard because it is expressed at a constitutive high level, and its expression does not show much variation in different cells.

For PCR amplification, the primer sequences were selected from the VEGF-B and β-actin genes as follows: VEGF-B sense: 5'-GCCATGTGTCACCTTCGCAG-3' (SEQ ID NO:19) VEGF-B antisense: 5'-TGTCCCTGGAA-GAACACAGCC-3' (SEQ ID NO:29) β-actin sense: 5'-CGGGAAATCGTGCGTGACAT-3' (SEQ ID NO:30) β-actin antisense: 5'-GGAGTTGAAGGTAGTTTCGTG-3' (SEQ ID NO:31) [β-actin sequences comprise nucleotides 2105-2125 and 2411-2432 from Ng et al., *Mol. Cell Biol.* 5:2720-732 (1985)]. An aliquot of 4 µl from the cDNA reaction product was heated to 94° C. for 5 minutes and used as a template for PCR amplification with 20 pmol of primers, 10×PCR buffer, 1 µl of 20 mM dNTPs and 2.5 U of Taq polymerase. Final volume was adjusted to 100 µl with DEPC treated water. Denaturation was at 95° C. for 1 minute, annealing at 62° C. for 45 seconds, and polymerization at 72° C. for 50 seconds, for a total of 35 cycles for VEGF-B and 25 cycles for β-actin. After every 5 cycles, 15 µl aliquots were taken for analysis.

Electrophoresis of 5 µl of the PCR reaction mix was performed in a 2% agarose gel containing ethidium bromide. The size marker DNA fragments ranged in length from 24 to 726 base pairs (ΦX174 DNA/Hinf I marker from Promega, Madison, Wis., USA). The tested samples thus included four metastatic melanomas, muscle, normal skin, a negative control (without reverse transcriptase), and the ΦX174 DNA/Hinf I size marker. The results of the RT-PCR analysis for VEGF-B (PCR product lengths 323 and 234 bp) and for β-actin show that VEGF-B is highly expressed in all melanomas studied, at levels approximately similar to the expression in muscle tissue. On the other hand, normal skin has very little of the VEGF-B RNA. Similar conclusions can be drawn from Northern blotting and hybridization analysis.

The foregoing results indicate that that VEGF-B is a novel growth factor for endothelial cells which plays a role in vascularization, in particular of muscle. Collateral artery growth in ischemic heart or limb may be promoted by arterial administration of a VEGF-B bolus using techniques described by Takeshita et al., *Am. J. Pathol.*, 147:1649-60 (1995). The cell-association of VEGF-B may have several implications for regulation of vascularization and endothelial cell growth. In developing embryos and in contractile tissues, cell-associated VEGF-B may provide spatial cues to outgrowing endothelial cells during establishment and maintenance of the vascular tree. It could also, through its cell-association, support the regeneration of damaged endothelium in adult vessels. Reendothelialization of arterial injury may be promoted by direct application of VEGF-B using techniques described by Asahara et al., *Circulation*, 91(11):2793-802 (1995). The ability of VEGF-B to modulate the secretion of VEGF by heterodimer formation suggests an indirect role of VEGF-B in VEGF signalling, thereby regulating receptor binding and/or activation as described by Potgens et al., *J. Biol. Chem.*, 269(52):32879-85 (1994). The formation of multiple heterodimeric complexes of these growth factors could provide a basis for a diverse array of regulatory signals for endothelial cells.

VEGF-B can be used as a growth factor for populations of endothelial cells in vitro. VEGF-B may be used to promote desirable angiogenesis, i.e. the formation of new blood vessels and capillaries; see Takeshita et al., supra. For example, it may be useful in promoting the development of the corpus luteum and endometrium as an aid to initiating and/or maintaining pregnancy. It would also be useful in bone repair by virtue of its action on endothelial cells. Administration of VEGF-B may also be useful in supporting embryogenesis, as well as somatic growth and vascular development and differentiation. Topical application of VEGF-B to wounds may be useful in promoting wound healing, and oral administration of VEGF-B may be useful to accelerate the healing of gastric and/or duodenal ulcers The ability of VEGF-B to modulate the secretion of VEGF by heterodimer formation could provide a therapeutic role for VEGF-B in diseases where VEGF agonists would be useful; see Potgens et al., supra.

VEGF-B may exert proliferative effects on mesodermal cells either directly or via improvements in the blood supply.

VEGF-B has been found to be overexpressed in tumors, such as melanomas. Consequently, assays for VEGF-B expression can be used as tools in tumor diagnosis, and suppression of VEGF-B expression, for example with monoclonal antibodies, may be useful to retard tumor growth.

Tumor assays for VEGF-B may be useful as indicators of metastatic risk. For example, use of VEGF-B antibodies analogous to the procedures described by Takahashi et al., *Cancer Res.*, 55:3964-68 (1995) in order to quantitate neovascularization and proliferation could be used as an indicator of metastatic risk from colon cancer. Assays of VEGF-B in body fluids or the tumor itself by histochemistry may be useful as a tumor prognostic factor. An ELISA analogous to the procedure described by Kondo et al., *Biochemica et Biophysica Acta*, 1221(2):211-14 (1994) may be useful to detect VEGF-B upregulation as a tumor screen. An enzyme linked immunoabsorbent assay of VEGF-B expression using techniques described by Boocock et al., *J. Natl. Cancer Inst.*, 87:506-16 (1995) may be useful as a diagnostic index of ovarian cancer. An assay of VEGF-B expression similar to the VEGF assay described by Weindel et al., *Neurosurgery*, 35:439-48 (1994) may be useful as an indicator of malignancy in brain tumors.

Furthermore, because tumor growth requires angiogenesis, administration of VEGF-B may also be useful in promoting tumor growth in laboratory animals in order to test anti-tumorigenic drugs. VEGF-B may also be useful to increase the microvascularity of hypoxic areas of tumors and make them more sensitive to radiation, radiation sensitizing drugs, etc.

The angiogenic action of VEGF-B may be useful in treating ischemic conditions. Administration of an intra-arterial bolus of VEGF-B by the techniques described in Bauters et al., *American Journal of Physiology*, 267(4 Pt 2):H1263-71 (1994) may be useful to treat lower extremity ischemia and increase perfusion in the extremities. Using procedures described by Mesri et al., *Circulation Research,* 76:161-67 (1995) an angiogenic response may be produced in tissue injected with fibroblast cells transduced with a virus which expresses VGEF-B in order to treat tissue ischemia (e.g. myocardial ischemia). VEGF-B or agonists could be used to stimulate the development of collateral circulation in cases of arterial and/or venous obstruction, e.g. myocardial infarcts, ischaemic limbs, deep venous thrombisis, and/or postpartum vascular problems; see Takeshita et al, supra.

A VEGF-B/VEGF-B receptor system may be used as an assay system to detect small molecules as agonists/antagonists for development as new drugs. Examples of small molecules which could be detected include, but are not limited to, organic chemicals, peptides, and RNA molecules.

Pharmaceutical compositions may be produced by admixing a pharmaceutically effective amount of VEGF-B protein with one or more suitable carriers or adjuvants such as water, mineral oil, polyethylene glycol, starch, talcum, lactose, thickeners, stabilizers, suspending agents, etc. Such compositions may be in the form of solutions, suspensions, tablets, capsules, creams, salves, ointments, or other conventional forms.

As demonstrated in Example 7, VEGF-B protein also can be used to produce antibodies. In general, conventional antibody production techniques may be used to produce VEGF-B antibodies. For example, specific monoclonal antibodies may be produced via immunization of fusion proteins obtained by recombinant DNA expression.

Labelled monoclonal antibodies, in particular, should be useful in screening for conditions associated with abnormal levels of VEGF-B in the body. For example, an assay of VEGF-B in synovial fluids and/or joint tissue by immunofluorometric techniques analogous to the the procedure described by Fava et al., *Journal of Experimental Medicine,* 180:341-46 (1994) may be useful as a diagnostic indicator of rheumatoid arthritis. A radioimmunoassay of VEGF-B in occular fluid using techniques described by Aiello et al., in *New England Journal of Medicine,* 331(22):1480-87 (1994) may be useful as a diagnostic indicator of diabetic retinopathy, neovascularization of the iris or retinal vein occlusion. Immunoassays of VEGF-B levels in blood, urine or other bodily fluids may be useful also as a tumor marker; see Kondo et al., supra. These monoclonal antibodies to VEGF-B also may be useful in inhibiting angiogenesis associated with high levels of VEGF-B in the body, e.g. in rapidly proliferating, angiogenesis-dependent tumors in mammals, and thereby may retard the growth of such tumors. Treatment with a monoclonal antibody specific for VEGF-B using techniques analogous to those described by Kim et al., in *Nature,* 362(6243):841-44 (1993) may be useful to suppress or inhibit tumor growth in vivo. Intravenous and/or subcutaneous injection of monoclonal antibodies to VEGF-B using procedures like those described by Asano et al., in *Cancer Research,* 55:5296-5301 (1995) may be useful to inhibit neovascularization and primary and metastatic growth of solid tumors. For the therapy of humans, chiaserization or humanization of such monoclonal antibodies is to be preferred. Treatment may be effected, e.g., by twice weekly intraperitoneal injection of 10 to 500 µg, preferably 50-100 µg of monoclonal antibody.

VEGF-B antagonists such as antibodies also may be useful to inhibit new blood vessels in diabetic retinopathy, psoriasis, arthopathies and/or vascular tumors such as haemangiomas; see Aiello et al., supra.

The foregoing description and examples have been set forth merely to illustrate the invention and are not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. An isolated processed VEGF-B polypeptide capable of promoting proliferation of endothelial cells or mesodermal cells, comprising an amino acid sequence selected from the group consisting of amino acids 22 to 188 of SEQ ID NO: 5, amino acids 22 to 195 of SEQ ID NO: 7, amino acids 22 to 133 of SEQ ID NO: 9, amino acids 22 to 188 of SEQ ID NO: 11, amino acids 22 to 207 of SEQ ID NO: 13 and amino acids 22 to 207 of SEQ ID NO: 15.

2. The processed VEGF-B polypeptide according to claim 1, which is a human sequence.

3. The processed VEGF-B polypeptide according to claim 1, which is a murine sequence.

4. The processed VEGF-B polypeptide according to claim 1, which comprises the amino acid sequence of amino acids 22 to 188 of SEQ ID NO: 5.

5. The processed VEGF-B polypeptide according to claim 1, which comprises the amino acid sequence of amino acids 22 to 195 of SEQ ID NO: 7.

6. The processed VEGF-B polypeptide according to claim 1, which comprises the amino acid sequence of amino acids 22 to 133 of SEQ ID NO: 9.

7. The processed VEGF-B polypeptide according to claim 1, which comprises the amino acid sequence of amino acids 22 to 188 of SEQ ID NO: 11.

8. A pharmaceutical composition comprising an effective endothelial or mesodermal cell proliferation-promoting amount of an isolated polypeptide according to claim 1, and at least one pharmaceutical carrier or diluent.

9. A pharmaceutical composition according to claim 8, further comprising heparin.

10. A pharmaceutical composition according to claim 9, further comprising vascular endothelial growth factor.

11. A pharmaceutical composition comprising an effective angiogenesis-stimulating amount of an isolated polypeptide according to claim 1, and heparin.

12. An isolated polypeptide dimer comprising a polypeptide according to claim 1.

13. An isolated polypeptide dimer according to claim 12, which is a homodimer.

14. An isolated polypeptide dimer according to claim 12, which is a heterodimer of said polypeptide and VEGF.

15. An isolated polypeptide dimer according to claim 12, which is a disulfide-linked dimer.

16. The processed VEGF-B polypeptide according to claim 1, which comprises the amino acid sequence of amino acids 22-207 of SEQ ID NO: 13 or amino acids 22-207 of SEQ ID NO: 15.

* * * * *

SEQUENCE LISTING (1) GENERAL INFORMATION:

(iii) NUMBER OF SEQUENCES: 57

(2) INFORMATION FOR SEQ ID NO: 1:

(i) SEQUENCE CHARACTERISTICS:
      (A) LENGTH: 886 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (vi) ORIGINAL SOURCE:
      (F) TISSUE TYPE: mouse embryo (vii) IMMEDIATE SOURCE:
      (B) CLONE: pcif2

(xi) SEQUENCE DESCRIPTION: SEQ ID NO: 1:

```
CGGGACGCCC AGTGGTGCCA TGGATAGACG TTTATGCACG TGCCACATGC CAGCCCAGGG      60

AGGTGGTGGT GCCTCTGAGC ATGGAACTCA TGGGCAATGT GGTCAAACAA CTAGTGCCCA     120

GCTGTGTGAC TGTGCAGCGC TGTGGTGGCT GCTGCCCTGA CGATGGCCTG GAATGTGTGC     180
```

-continued

```
CCACTGGGCA ACACCAAGTC CGAATGCAGA TCCTCATGAT CCAGTACCCG AGCAGTCAGC      240

TGGGGGAGAT GTCCCTGGAA GAACACAGCC AATGTGAATG CAGACCAAAA AAAAAAAGGA      300

GAGTGCTGTG AAGCCAGACA GCCCCAGGAT CCTCTGCCCG CCTTGCACCC AGCGCCGTCA      360

ACGCCCTGAC CCCCGGACCT GCCGCTGCCG CTGCAGACGC CGCCGCTTCC TCCATTGCCA      420

AGGGCGGGGC TTAGAGCTCA ACCCAGACAC CTGTAGGTGC CGGAAGCCGC GAAAGTGACA      480

AGCTGCTTTC CAGACTCCAC GGGCCCGGCT GCTTTTATGG CCCTGCTTCA CAGGGACGAA      540

GAGTGGAGCA CAGGCAAACC TCCTCAGTCT GGGAGGTCAC TGCCCCAGGA CCTGGACCTT      600

TTAGAGAGCT CTCTCGCCAT CTTTTATCTC CCAGAGCTGC CATCTAACAA TTGTCAAGGA      660

ACCTCATGTC TCACCTCAGG GGCCAGGGTA CTCTCTCACT TAACCACCCT GGTCAAGTGA      720

GCATCTTCTG GCTGGCTGTC TCCCCTCACT ATGAAAACCC CAAACTTCTA CCAATAACGG      780

GATTTGGGTT CTGTTATGAT AACTGTGACA CACACACACA CTCACACTCT GATAAAAGAG      840

AACTCTGATA AAGAGATGG AAGACACTAA AAAAAAAAA AAAAA                        886
```

(2) INFORMATION FOR SEQ ID NO: 2:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (F) TISSUE TYPE: mouse embryo (xi) SEQUENCE DESCRIPTION: SEQ ID NO: 2:

```
Gly Arg Pro Val Val Pro Trp Ile Asp Val Tyr Ala Arg Ala Thr Cys
1               5                  10                  15

Gln Pro Arg Glu Val Val Pro Leu Ser Met Glu Leu Met Gly Asn
            20                  25                  30

Val Val Lys Gln Leu Val Pro Ser Cys Val Thr Val Gln Arg Cys Gly
        35                  40                  45

Gly Cys Cys Pro Asp Asp Gly Leu Glu Cys Val Pro Thr Gly Gln His
    50                  55                  60

Gln Val Arg Met Gln Ile Leu Met Ile Gln Tyr Pro Ser Ser Gln Leu
65                  70                  75                  80

Gly Glu Met Ser Leu Glu Glu His Ser Gln Cys Glu Cys Arg Pro Lys
                85                  90                  95

Lys Lys Arg Arg Val Leu
            100
```

(2) INFORMATION FOR SEQ ID NO: 3:

(i) SEQUENCE CHARACTERISTICS:
        (A) LENGTH: 55 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (F) TISSUE TYPE: mouse embryo (xi) SEQUENCE DESCRIPTION: SEQ ID NO: 3:

Lys Pro Asp Ser Pro Arg Ile Leu Cys Pro Pro Cys Thr Gln Arg Arg
1               5                   10                  15

Gln Arg Pro Asp Pro Arg Thr Cys Arg Cys Arg Cys Arg Arg Arg
            20                  25                  30

Phe Leu His Cys Gln Gly Arg Gly Leu Glu Leu Asn Pro Asp Thr Cys
            35                  40                  45

Arg Cys Arg Lys Pro Arg Lys
        50                  55

(2) INFORMATION FOR SEQ ID NO: 4:

(i) SEQUENCE CHARACTERISTICS:
        (A) LENGTH: 565 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
        (F) TISSUE TYPE: adult mouse heart (xi) SEQUENCE DESCRIPTION: SEQ ID NO: 4:

```
GAGCCCCCTG CTCCGTCGCC TGCTGCTTGT TGCACTGCTG CAGCTGGCTC GCACCCAGGC    60
CCCTGTGTCC CAGTTTGATG GCCCCAGCCA CCAGAAGAAA GTGGTGCCAT GGATAGACGT   120
TTATGCACGT GCCACATGCC AGCCCAGGGA GGTGGTGGTG CCTCTGAGCA TGGAACTCAT   180
GGGCAATGTG GTCAAACAAC TAGTGCCCAG CTGTGTGACT GTGCAGCGCT GTGGTGGCTG   240
CTGCCCTGAC GATGGCCTGG AATGTGTGCC CACTGGGCAA CACCAAGTCC GAATGCAGAT   300
CCTCATGATC CAGTACCCGA GCAGTCAGCT GGGGGAGATG TCCCTGGAAG AACACAGCCA   360
ATGTGAATGC AGACCAAAAA AAAAGGAGAG TGCTGTGAAG CCAGACAGCC CCAGGATCCT   420
CTGCCCCGCCT TGCACCCAGC GCCGTCAACG CCCTGACCCC CGGACCTGCC GCTGCCGCTG   480
CAGACGCCGC CGCTTCCTCC ATTGCCAAGG GCGGGGCTTA GAGCTCAACC CAGACACCTG   540
TAGGTGCCGG AAGCCGCGAA AGTGA                                         565
```

(2) INFORMATION FOR SEQ ID NO: 5:

(i) SEQUENCE CHARACTERISTICS:
        (A) LENGTH: 188 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (F) TISSUE TYPE: adult mouse heart (xi) SEQUENCE DESCRIPTION: SEQ ID NO: 5:

Met Ser Pro Leu Leu Arg Arg Leu Leu Leu Val Ala Leu Leu Gln Leu
1               5                   10                  15

Ala Arg Thr Gln Ala Pro Val Ser Gln Phe Asp Gly Pro Ser His Gln
            20                  25                  30

Lys Lys Val Val Pro Trp Ile Asp Val Tyr Ala Arg Ala Thr Cys Gln
            35                  40                  45

```
Pro Arg Glu Val Val Pro Leu Ser Met Glu Leu Met Gly Asn Val
        50                  55                  60

Val Lys Gln Leu Val Pro Ser Cys Val Thr Val Gln Arg Cys Gly Gly
65                  70                  75                  80

Cys Cys Pro Asp Asp Gly Leu Glu Cys Val Pro Thr Gly Gln His Gln
                85                  90                  95

Val Arg Met Gln Ile Leu Met Ile Gln Tyr Pro Ser Ser Gln Leu Gly
            100                 105                 110

Glu Met Ser Leu Glu Glu His Ser Gln Cys Glu Cys Arg Pro Lys Lys
            115                 120                 125

Lys Glu Ser Ala Val Lys Pro Asp Ser Pro Arg Ile Leu Cys Pro Pro
        130                 135                 140

Cys Thr Gln Arg Arg Gln Arg Pro Asp Pro Thr Cys Arg Cys Arg
145                 150                 155                 160

Cys Arg Arg Arg Phe Leu His Cys Gln Gly Arg Gly Leu Glu Leu
                165                 170                 175

Asn Pro Asp Thr Cys Arg Cys Arg Lys Pro Arg Lys
            180                 185
```

(2) INFORMATION FOR SEQ ID NO: 6:

(i) SEQUENCE CHARACTERISTICS:
        (A) LENGTH: 591 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
        (F) TISSUE TYPE: adult mouse heart (xi) SEQUENCE DESCRIPTION: SEQ ID NO: 6:

```
ACCATGAGCC CCCTGCTCCG TCGCCTGCTG CTTGTTGCAC TGCTGCAGCT GGCTCGCACC     60
CAGGCCCCTG TGTCCCAGTT TGATGGCCCC AGCCACCAGA AGAAAGTGGT GCCATGGATA    120
GACGTTTATG CACGTGCCAC ATGCCAGCCC AGGGAGGTGG TGGTGCCTCT GAGCATGGAA    180
CTCATGGGCA ATGTGGTCAA ACAACTAGTG CCCAGCTGTG TGACTGTGCA GCGCTGTGGT    240
GGCTGCTGCC CTGACGATGG CCTGGAATGT GTGCCCACTG GCAACACCA AGTCCGAATG     300
CAGGTACCAG GGCCTATGGG TCAGATCCTC ATGATCCAGT ACCCGAGCAG TCAGCTGGGG    360
GAGATGTCCC TGGAAGAACA CAGCCAATGT GAATGCAGAC CAAAAAAAAA GGAGAGTGCT    420
GTGAAGCCAG ACAGCCCCAG GATCCTCTGC CCGCCTTGCA CCCAGCGCCG TCAACGCCCT    480
GACCCCCGGA CCTGCCGCTG CCGCTGCAGA CGCCGCCGCT TCCTCCATTG CCAAGGGCGG    540
GGCTTAGAGC TCAACCCAGA CACCTGTAGG TGCCGGAAGC CGCGAAAGTG A             591
```

(2) INFORMATION FOR SEQ ID NO: 7:

(i) SEQUENCE CHARACTERISTICS:
        (A) LENGTH: 195 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
    (F) TISSUE TYPE: adult mouse heart (xi) SEQUENCE DESCRIPTION: SEQ ID NO: 7:

```
Met Ser Pro Leu Leu Arg Arg Leu Leu Leu Val Ala Leu Leu Gln Leu
1               5                   10                  15

Ala Arg Thr Gln Ala Pro Val Ser Gln Phe Asp Gly Pro Ser His Gln
            20                  25                  30

Lys Lys Val Val Pro Trp Ile Asp Val Tyr Ala Arg Ala Thr Cys Gln
            35                  40                  45

Pro Arg Glu Val Val Pro Leu Ser Met Glu Leu Met Gly Asn Val
50                      55                  60

Val Lys Gln Leu Val Pro Ser Cys Val Thr Val Gln Arg Cys Gly Gly
65                  70                  75                  80

Cys Cys Pro Asp Asp Gly Leu Glu Cys Val Pro Thr Gly Gln His Gln
                85                  90                  95

Val Arg Met Gln Val Pro Gly Pro Met Gly Gln Ile Leu Met Ile Gln
                100                 105                 110

Tyr Pro Ser Ser Gln Leu Gly Glu Met Ser Leu Glu Glu His Ser Gln
            115                 120                 125

Cys Glu Cys Arg Pro Lys Lys Lys Glu Ser Ala Val Lys Pro Asp Ser
130                     135                 140

Pro Arg Ile Leu Cys Pro Pro Cys Thr Gln Arg Arg Gln Arg Pro Asp
145                 150                 155                 160

Pro Arg Thr Cys Arg Cys Arg Cys Arg Arg Arg Phe Leu His Cys
                165                 170                 175

Gln Gly Arg Gly Leu Glu Leu Asn Pro Asp Thr Cys Arg Cys Arg Lys
            180                 185                 190

Pro Arg Lys
    195
```

(2) INFORMATION FOR SEQ ID NO: 8:

(i) SEQUENCE CHARACTERISTICS:
        (A) LENGTH: 405 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 8:

```
ACCATGAGCC CCCTGCTCCG TCGCCTGCTG CTTGTTGCAC TGCTGCAGCT GGCTCGCACC    60

CAGGCCCCTG TGTCCCAGTT TGATGGCCCC AGCCACCAGA AGAAAGTGGT GCCATGGATA   120

GACGTTTATG CACGTGCCAC ATGCCAGCCC AGGGAGGTGG TGGTGCCTCT GAGCATGGAA   180

CTCATGGGCA ATGTGGTCAA ACAACTAGTG CCCAGCTGTG TGACTGTGCA GCGCTGTGGT   240

GGCTGCTGCC CTGACGATGG CCTGGAATGT GTGCCCACTG GCAACACCA AGTCCGAATG    300

CAGATCCTCA TGATCCAGTA CCCGAGCAGT CAGCTGGGGG AGATGTCCCT GGAAGAACAC   360

AGCCAATGTG AATGCAGACC AAAAAAAAAA AGGAGAGTGC TGTGA                   405
```

(2) INFORMATION FOR SEQ ID NO: 9:

(i) SEQUENCE CHARACTERISTICS:
        (A) LENGTH: 133 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 9:

```
Met Ser Pro Leu Leu Arg Arg Leu Leu Val Ala Leu Leu Gln Leu
1               5                   10                  15

Ala Arg Thr Gln Ala Pro Val Ser Gln Phe Asp Gly Pro Ser His Gln
            20                  25                  30

Lys Lys Val Val Pro Trp Ile Asp Val Tyr Ala Arg Ala Thr Cys Gln
                35                  40                  45

Pro Arg Glu Val Val Pro Leu Ser Met Glu Leu Met Gly Asn Val
50                      55                  60

Val Lys Gln Leu Val Pro Ser Cys Val Thr Val Gln Arg Cys Gly Gly
65                  70                  75                  80

Cys Cys Pro Asp Asp Gly Leu Glu Cys Val Pro Thr Gly Gln His Gln
                85                  90                  95

Val Arg Met Gln Ile Leu Met Ile Gln Tyr Pro Ser Ser Gln Leu Gly
                100                 105                 110

Glu Met Ser Leu Glu Glu His Ser Gln Cys Glu Cys Arg Pro Lys Lys
            115                 120                 125

Lys Arg Arg Val Leu
        130
```

(2) INFORMATION FOR SEQ ID NO: 10:

(i) SEQUENCE CHARACTERISTICS:
        (A) LENGTH: 570 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
        (F) TISSUE TYPE: human fibrosarcoma (xi) SEQUENCE DESCRIPTION: SEQ ID NO: 10:

```
ACCATGAGCC CTCTGCTCCG CCGCCTGCTG CTCGCCGCAC TCCTGCAGCT GGCCCCCGCC      60
CAGGCCCCTG TCTCCCAGCC TGATGCCCCT GGCCACCAGA GGAAAGTGGT GTCATGGATA     120
GATGTGTATA CTCGCGCTAC CTGCCAGCCC CGGGAGGTGG TGGTGCCCTT GACTGTGGAG     180
CTCATGGGCA CCGTGGCCAA ACAGCTGGTG CCCAGCTGCG TGACTGTGCA GCGCTGTGGT     240
GGCTGCTGCC CTGACGATGG CCTGGAGTGT GTGCCCACTG GCCAGCACCA AGTCCGGATG     300
CAGATCCTCA TGATCCGGTA CCCGAGCAGT CAGCTGGGGG AGATGTCCCT GGAAGAACAC     360
AGCCAGTGTG AATGCAGACC TAAAAAAAAG ACAGTGCTG TGAAGCCAGA CAGCCCCAGG     420
CCCCTCTGCC CACGCTGCAC CCAGCACCAC CAGCGCCCTG ACCCCGGAC CTGCCGCTGC     480
CGCTGCCGAC GCCGCAGCTT CCTCCGTTGC CAAGGGCGGG GCTTAGAGCT CAACCCAGAC     540
ACCTGCAGGT GCCGGAAGCT GCGAAGGTGA                                     570
```

(2) INFORMATION FOR SEQ ID NO: 11:

(i) SEQUENCE CHARACTERISTICS:
        (A) LENGTH: 188 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
(F) TISSUE TYPE: human fibrosarcoma (xi) SEQUENCE DESCRIPTION: SEQ ID NO: 11:

```
Met Ser Pro Leu Leu Arg Arg Leu Leu Leu Ala Ala Leu Leu Gln Leu
1               5                   10                  15

Ala Pro Ala Gln Ala Pro Val Ser Gln Pro Asp Ala Pro Gly His Gln
            20                  25                  30

Arg Lys Val Val Ser Trp Ile Asp Val Tyr Thr Arg Ala Thr Cys Gln
        35                  40                  45

Pro Arg Glu Val Val Pro Leu Thr Val Glu Leu Met Gly Thr Val
    50                  55                  60

Ala Lys Gln Leu Val Pro Ser Cys Val Thr Val Gln Arg Cys Gly Gly
65                  70                  75                  80

Cys Cys Pro Asp Asp Gly Leu Glu Cys Val Pro Thr Gly Gln His Gln
                85                  90                  95

Val Arg Met Gln Ile Leu Met Ile Arg Tyr Pro Ser Ser Gln Leu Gly
            100                 105                 110

Glu Met Ser Leu Glu Glu His Ser Gln Cys Glu Cys Arg Pro Lys Lys
        115                 120                 125

Lys Asp Ser Ala Val Lys Pro Asp Ser Pro Arg Pro Leu Cys Pro Arg
    130                 135                 140

Cys Thr Gln His His Gln Arg Pro Asp Pro Arg Thr Cys Arg Cys Arg
145                 150                 155                 160

Cys Arg Arg Arg Ser Phe Leu Arg Cys Gln Gly Arg Gly Leu Glu Leu
                165                 170                 175

Asn Pro Asp Thr Cys Arg Cys Arg Lys Leu Arg Arg
            180                 185
```

(2) INFORMATION FOR SEQ ID NO: 12:

(i) SEQUENCE CHARACTERISTICS:
(A) LENGTH: 624 base pairs
(B) TYPE: nucleic acid
(C) STRANDEDNESS: single
(D) TOPOLOGY: linear (ii) MOLECULE TYPE: cDNA (iii) HYPOTHETICAL: NO (vi) ORIGINAL SOURCE:
(F) TISSUE TYPE: mouse (xi) SEQUENCE DESCRIPTION: SEQ ID NO: 12:

```
ATGAGCCCCC TGCTCCGTCG CCTGCTGCTT GTTGCACTGC TGCAGCTGGC TCGCACCCAG      60

GCCCCTGTGT CCCAGTTTGA TGGCCCCAGC CACCAGAAGA AGTGGTGCC ATGGATAGAC      120

GTTTATGCAC GTGCCACATG CCAGCCCAGG GAGGTGGTGG TGCCTCTGAG CATGGAACTC     180

ATGGGCAATG TGGTCAAACA ACTAGTGCCC AGCTGTGTGA CTGTGCAGCG CTGTGGTGGC     240

TGCTGCCCTG ACGATGGCCT GGAATGTGTG CCCACTGGGC AACACCAAGT CCGAATGCAG     300

ATCCTCATGA TCCAGTACCC GAGCAGTCAG CTGGGGGAGA TGTCCCTGGA AGAACACAGC     360

CAATGTGAAT GCAGACCAAA AAAAAAGGAG AGTGCTGTGA AGCCAGACAG GGTTGCCATA     420

CCCCACCACC GTCCCCAGCC CCGCTCTGTT CCGGGCTGGG ACTCTACCCC GGGAGCATCC     480
```

```
TCCCCAGCTG ACATCATCCA TCCCACTCCA GCCCCAGGAT CCTCTGCCCG CCTTGCACCC      540

AGCGCCGTCA ACGCCCTGAC CCCCGGACCT GCCGCTGCCG CTGCAGACGC CGCCGCTTCC      600

TCCATTGCCA AGGGCGGGGC TTAG                                              624
```

(2) INFORMATION FOR SEQ ID NO: 13:

(i) SEQUENCE CHARACTERISTICS:
        (A) LENGTH: 207 amino acids
        (B) TYPE: amino acid
        (D) TOPOLOGY: linear (ii) MOLECULE TYPE: protein (vi) ORIGINAL SOURCE:
        (F) TISSUE TYPE: mouse (xi) SEQUENCE DESCRIPTION: SEQ ID NO: 13:

```
Met Ser Pro Leu Leu Arg Arg Leu Leu Leu Val Ala Leu Leu Gln Leu
 1               5                  10                  15

Ala Arg Thr Gln Ala Pro Val Ala Gln Phe Asp Gly Pro Ser His Gln
            20                  25                  30

Lys Lys Val Val Pro Trp Ile Asp Val Tyr Ala Arg Ala Thr Cys Gln
        35                  40                  45

Pro Arg Glu Val Val Pro Leu Ser Met Glu Leu Met Gly Asn Val
    50                  55                  60

Val Lys Gln Leu Val Pro Ser Cys Val Thr Val Gln Arg Cys Gly Gly
65                  70                  75                  80

Cys Cys Pro Asp Asp Gly Leu Glu Cys Val Pro Thr Gly Gln His Gln
                85                  90                  95

Val Arg Met Gln Ile Leu Met Ile Gln Tyr Pro Ser Ser Gln Leu Gly
            100                 105                 110

Glu Met Ser Leu Glu Glu His Ser Gln Cys Glu Cys Arg Pro Lys Lys
        115                 120                 125

Lys Glu Ser Ala Val Lys Pro Asp Arg Val Ala Ile Pro His His Arg
    130                 135                 140

Pro Gln Pro Arg Ser Val Pro Gly Trp Asp Ser Thr Pro Gly Ala Ser
145                 150                 155                 160

Ser Pro Ala Asp Ile Ile His Pro Thr Pro Ala Pro Gly Ser Ser Ala
                165                 170                 175

Arg Leu Ala Pro Ser Ala Val Asn Ala Leu Thr Pro Gly Pro Ala Ala
            180                 185                 190

Ala Ala Ala Asp Ala Ala Ala Ser Ser Ile Ala Lys Gly Gly Ala
        195                 200                 205
```

(2) INFORMATION FOR SEQ ID NO: 14:

(i) SEQUENCE CHARACTERISTICS:
        (A) LENGTH: 624 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (F) TISSUE TYPE: human (xi) SEQUENCE DESCRIPTION: SEQ ID NO: 14:

```
ATGAGCCCTC TGCTCCGCCG CCTGCTGCTC GCCGCACTCC TGCAGCTGGC CCCCGCCCAG      60

GCCCCTGTCT CCCAGCCTGA TGCCCCTGGC CACCAGAGGA AAGTGGTGTC ATGGATAGAT     120
```

-continued

```
GTGTATACTC GCGCTACCTG CCAGCCCCGG GAGGTGGTGG TGCCCTTGAC TGTGGAGCTC      180

ATGGGCACCG TGGCCAAACA GCTGGTGCCC AGCTGCGTGA CTGTGCAGCG CTGTGGTGGC      240

TGCTGCCCTG ACGATGGCCT GGAGTGTGTG CCCACTGGGC AGCACCAAGT CCGGATGCAG      300

ATCCTCATGA TCCGGTACCC GAGCAGTCAG CTGGGGGAGA TGTCCCTGGA AGAACACAGC      360

CAGTGTGAAT GCAGACCTAA AAAAAAGGAC AGTGCTGTGA AGCCAGACAG GGCTGCCACT      420

CCCCACCACC GTCCCCAGCC CCGTTCTGTT CCGGGCTGGG ACTCTGCCCC CGGAGCACCC      480

TCCCCAGCTG ACATCACCCA TCCCACTCCA GCCCCAGGCC CCTCTGCCCA CGCTGCACCC      540

AGCACCACCA GCGCCCTGAC CCCCGGACCT GCCGCCGCCG CTGCCGACGC CGCAGCTTCC      600

TCCGTTGCCA AGGGCGGGGC TTAG                                              624
```

(2) INFORMATION FOR SEQ ID NO: 15:

(i) SEQUENCE CHARACTERISTICS:
        (A) LENGTH: 207 amino acids
        (B) TYPE: amino acid
        (C) STRANDEDNESS: single
        (D) TOPOLOGY: linear (ii) MOLECULE TYPE: protein (vi) ORIGINAL SOURCE:
        (F) TISSUE TYPE: human (xi) SEQUENCE DESCRIPTION: SEQ ID NO: 15:

```
Met Ser Pro Leu Leu Arg Arg Leu Leu Leu Ala Ala Leu Leu Gln Leu
1               5                   10                  15

Ala Pro Ala Gln Ala Pro Val Ser Gln Pro Asp Ala Pro Gly His Gln
            20                  25                  30

Arg Lys Val Val Ser Trp Ile Asp Val Tyr Thr Arg Ala Thr Cys Gln
        35                  40                  45

Pro Arg Glu Val Val Val Pro Leu Thr Val Glu Leu Met Gly Thr Val
    50                  55                  60

Ala Lys Gln Leu Val Pro Ser Cys Val Thr Val Gln Arg Cys Gly Gly
65                  70                  75                  80

Cys Cys Pro Asp Asp Gly Leu Glu Cys Val Pro Thr Gly Gln His Gln
                85                  90                  95

Val Arg Met Gln Ile Leu Met Ile Arg Tyr Pro Ser Ser Gln Leu Gly
            100                 105                 110

Glu Met Ser Leu Glu Glu His Ser Gln Cys Glu Cys Arg Pro Lys Lys
        115                 120                 125

Lys Asp Ser Ala Val Lys Pro Asp Arg Ala Ala Thr Pro His His Arg
    130                 135                 140

Pro Gln Pro Arg Ser Val Pro Gly Trp Asp Ser Ala Pro Gly Ala Pro
145                 150                 155                 160

Ser Pro Ala Asp Ile Thr His Pro Thr Pro Ala Pro Gly Pro Ser Ala
                165                 170                 175

His Ala Ala Pro Ser Thr Thr Ser Ala Leu Thr Pro Gly Pro Ala Ala
            180                 185                 190

Ala Ala Ala Asp Ala Ala Ala Ser Ser Val Ala Lys Gly Gly Ala
        195                 200                 205
```

(2) INFORMATION FOR SEQ ID NO: 16:

(i) SEQUENCE CHARACTERISTICS:
        (A) LENGTH: 13 amino acids (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 16:

Pro Xaa Cys Val Xaa Xaa Xaa Arg Cys Xaa Gly Cys Cys
1               5                   10

(2) INFORMATION FOR SEQ ID NO: 17:

(i) SEQUENCE CHARACTERISTICS:
            (A) LENGTH: 1550 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 17:

```
CTCGAGATCT GTTTGTTGTC TTGGAACAAT ACGGTTTAGA GGTGACTGGC GGGTGACGAG     60

AACATATGCG AGTTCACCTA AGAGAAAAGC TGAATGAGGC AATGCCTCTT CCTGACCATA    120

TCTCTTACTC AGATAACTAT AGAATTTATT GTCCAGTAAA GGGTATATTA AAAAATCATA    180

TTAAAAGTCA TACAGTGAAG TTGTCCAGGG AAATCAAGAC TTAACAGTCT CACTCTGACA    240

ATAATGAACA GGGGGATTCC CTCAAGATAG ACTAGGACAT GACCCCACAC TGGCAGGTAG    300

TAGTACCAGA AAAGAACGCA TGGAAAATCT TTACCTTATG CTTGAGGTAG GGACCAGGCT    360

AAAGTGAAGG CCAGACCTAA AATTCTATCT AAAATAAATC CACAATCGAA GAAAATATGT    420

GGTGTACAGG TATAGAATGT CTTTACTGGA TCATTGAAAT AGTAAGATAA ATTCAACTTT    480

TTACATTGTT TTCTTTTCCT CCAGTTAGGG CTTGAGACCT TCGTCTCTGG AGAGTGACTG    540

TCAATTGGAG CCCTGCTTTC TGGGTTTCTG GCCAGGGGGG TTGTGGATGC TTAACATGTG    600

CCTTTCACAG GACACTTCCT TACCCCAGCA GTGGCCANGT GTGCATCCCA CGACCAGGCC    660

TCCCTCTCAC GGAACATCTG TTGAGACTAG GAGATGCCTG GTGACTGTTG CCTGACCTGT    720

GTCCTGTGTA TTTCTGACAA GAGCCACTCT CAAAGACCCT GGCCAGGAGG AGAGTTAGGT    780

TCCAGTGTAG GTCAGCTCAG ACAGATGGAG GCCACAGAAN CAAACATGGG AAATCACAGA    840

AGTAGGTTTA TTACTCACAG ATCCCTATCC CAACCACCCA GGTGCCCTCT CCTCCAGGGC    900

CAACAGAGGC ATCCTTCAGC AGGAGCGACA ACGGCTAGGG CAGCGGCAAG CCGCCACCAT    960

CCGAGCCAAC CCAGGCCCCG AGATCGTGCC CCGGGGCGCC GGCCCCTGAG GGGCTCACCT   1020

GGATGGGGCC TGCATGCGTT CCCGCTTTGC TTCCTTCCCT GGACGGCCCG CTCCCCCGAA   1080

ACGCGCCGCC AATAAAGTGA TTCGCAGAGC TCGTGTGCGG CTCCCTCCTT AAGGCCCGAC   1140

GCCCCCGGCC CCGGCCTCGC CAAGGGCAGC GCCCCGGCCT CCGGGTAGTG GCGGCCGGCG   1200

ACTGGGGAGC CCAGCCTCCT GGGCGGTGCG TCCCCTTCCC CCTGCCGCGG CGGGAGGCGG   1260

GAGGGGGTGT GTGGAGGAGG CGGGCCCCGC CGACGGCCTC GCCCCCCCAC CCGCCGCCCC   1320

CGCCCCCGCC CCACGGGCCC GGTGGGGAGC GCGTGTCTGG GTCACATGAG CCGCCTGCCC   1380

GCCAGCCCGG GCCCAGCCCC CCGCCGCCCC CGCCGTCCCC GCCGCCGCTG CCCGCCGCCA   1440

CCGGCCGCCC GCCCGCCCGG CTCCTCCGGC CGCCTTCGCT GCGCTGCNTG CGCTGCCTGC   1500

ACCCAGGGCT CGGGAGGGGG CCGCGGAGGA GCCGCCCCCC GCGCCCGGCC             1550
```

(2) INFORMATION FOR SEQ ID NO: 18:

-continued

```
    (i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 18:

CACCATGAGC CCTCTGCTCC                                               20

(2) INFORMATION FOR SEQ ID NO: 19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 19:

GCCATGTGTC ACCTTCGCAG                                               20

(2) INFORMATION FOR SEQ ID NO: 20:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 20:

GGGCATCAGG CTGGGAGACA G                                             21

(2) INFORMATION FOR SEQ ID NO: 21:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 21:

Cys Pro Val Ser Gln Phe Asp Gly Pro Ser His Gln Lys Lys Val Val
1               5                   10                  15

Pro Cys (2) INFORMATION FOR SEQ ID NO: 22:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 22:

Ser Gln Pro Asp Ala Pro Gly His Gln Arg Lys Val Val Ser Trp Ile
1               5                   10                  15

Asp Val Tyr Thr Arg Ala Thr
            20
```

(2) INFORMATION FOR SEQ ID NO: 23:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 23:

CACAGCCAAT GTGAATGCA                                            19

(2) INFORMATION FOR SEQ ID NO: 24:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 24:

GCTCTAAGCC CCGCCCTTGG CAATGGAGGA A                          31

(2) INFORMATION FOR SEQ ID NO: 25:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 25:

ACGTAGATCT TCACTTTCGC GGCTTCCG                                28

(2) INFORMATION FOR SEQ ID NO: 26:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 26:

CTCTGTTCCG GGCTGGGACT CTA                                      23

(2) INFORMATION FOR SEQ ID NO: 27:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 27:

TCAGGGCGTT GACGGCGCTG GGTGCAA                               27

(2) INFORMATION FOR SEQ ID NO: 28:

(i) SEQUENCE CHARACTERISTICS:

(A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 28:

CCTGACGATG GCCTGGAGTG T                                              21

(2) INFORMATION FOR SEQ ID NO: 29:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 29:

TGTCCCTGGA AGAACACAGC C                                              21

(2) INFORMATION FOR SEQ ID NO: 30:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 30:

CGGGAAATCG TGCGTGACAT                                                20

(2) INFORMATION FOR SEQ ID NO: 31:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 31:

GGAGTTGAAG GTAGTTTCGT G                                              21

(2) INFORMATION FOR SEQ ID NO: 32:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO: 32:

TCGCACCCAG GTACGTGCGT                                                20

(2) INFORMATION FOR SEQ ID NO: 33:

(i) SEQUENCE CHARACTERISTICS:
        (A) LENGTH: 20 base pairs
        (B) TYPE: nucleic acid

```
            (C) STRANDEDNESS: single
            (D) TOPOLOGY: linear (ii) MOLECULE TYPE: DNA (genomic)

(xi) SEQUENCE DESCRIPTION: SEQ ID NO: 33:

TTTCCCACAG GCCCCTGTGT                                           20

(2) INFORMATION FOR SEQ ID NO: 34:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 34:

CAGAAGAAAG GTAATAATAG                                           20

(2) INFORMATION FOR SEQ ID NO: 35:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 35:

CTGCCCACAG TGGTGCCATG                                           20

(2) INFORMATION FOR SEQ ID NO: 36:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 36:

CCGAATGCAG GTACCAGGGC                                           20

(2) INFORMATION FOR SEQ ID NO: 37:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 37:

CTGAGCACAG ATCCTCATGA                                           20

(2) INFORMATION FOR SEQ ID NO: 38:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)
```

(xi) SEQUENCE DESCRIPTION: SEQ ID NO: 38:

GTGAATGCAG GTGCCAGCCA                                               20

(2) INFORMATION FOR SEQ ID NO: 39:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 39:

CTCCTCCTAG GGTTGCCATA                                               20

(2) INFORMATION FOR SEQ ID NO: 40:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 40:

AGCCAGACAG GTGAGTTTTT                                               20

(2) INFORMATION FOR SEQ ID NO: 41:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 41:

CTCCTCCTAG GGTTGCCATA                                               20

(2) INFORMATION FOR SEQ ID NO: 42:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 42:

CCCACTCCAG CCCCAGGATA                                               20

(2) INFORMATION FOR SEQ ID NO: 43:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 43:

ACACCTGTAG GTAAGGAGTC                                               20

(2) INFORMATION FOR SEQ ID NO: 44:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 44:

CACTCCCCAG GTGCCGGAAG                                      20

(2) INFORMATION FOR SEQ ID NO: 45:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 45:

CCCCGCCCAG GTACGTGCGG                                      20

(2) INFORMATION FOR SEQ ID NO: 46:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 46:

TCTCCCACAG GCCCCTGTCT                                      20

(2) INFORMATION FOR SEQ ID NO: 47:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 47:

CAGAGGAAAG GTAATACTTA                                      20

(2) INFORMATION FOR SEQ ID NO: 48:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 48:

CTGCTCCCAG TGGTGTCATG                                      20

(2) INFORMATION FOR SEQ ID NO: 49:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 49:

CCGGATGCAG GTACTGGGCA                                                         20

(2) INFORMATION FOR SEQ ID NO: 50:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 50:

CTGAGCACAG ATCCTCATGA                                                         20

(2) INFORMATION FOR SEQ ID NO: 51:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 51:

GTGAATGCAG GTGCCAGCCA                                                         20

(2) INFORMATION FOR SEQ ID NO: 52:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 52:

TACTTTTCAG ACCTAAAAAA                                                         20

(2) INFORMATION FOR SEQ ID NO: 53:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 53:

AGCCAGACAG GTGAGTCTTT                                                         20

(2) INFORMATION FOR SEQ ID NO: 54:

(i) SEQUENCE CHARACTERISTICS:
            (A) LENGTH: 20 base pairs
            (B) TYPE: nucleic acid
            (C) STRANDEDNESS: single -continued (D) TOPOLOGY: linear (ii) MOLECULE TYPE: DNA (genomic)

(xi) SEQUENCE DESCRIPTION: SEQ ID NO: 54:

TCCTCCCTAG GGCTGCCACT                                                    20

(2) INFORMATION FOR SEQ ID NO: 55:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 55:

CCCACTCCAG CCCCAGGCCC                                                    20

(2) INFORMATION FOR SEQ ID NO: 56:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 56:

ACACCTGCAG GTAGGTTTGG                                                    20

(2) INFORMATION FOR SEQ ID NO: 57:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 57:

CCCTCCTCAG GTGCCGGAAG                                                    20